United States Patent [19]

Rubin et al.

[11] Patent Number: 5,747,275
[45] Date of Patent: May 5, 1998

[54] PROTEIN KINASE REQUIRED FOR RAS SIGNAL TRANSDUCTION

[75] Inventors: Gerry Rubin, Berkeley; Marc Therrien, Union City; Henry Chang, Berkeley; Felix Karim, El Cerrito; David Wassarman, San Francisco, all of Calif.

[73] Assignee: The Regents of the University of California, Oakland, Calif.

[21] Appl. No.: 909,984

[22] Filed: Aug. 12, 1997

Related U.S. Application Data

[62] Division of Ser. No. 571,758, Dec. 13, 1995, Pat. No. 5,700,675.

[51] Int. Cl.$^6$ .............. C12Q 1/48; C12P 21/06; C07K 1/00; C07H 21/04
[52] U.S. Cl. ............ 435/15; 435/69.1; 435/252.3; 435/320.1; 530/350; 536/23.1; 536/23.5
[58] Field of Search ............ 435/15, 69.1, 252.3, 435/320.1; 530/350; 536/23.1, 23.5

[56] References Cited

PUBLICATIONS

Downward et al. (1995). Cell 83:831–834, 1995.

*Primary Examiner*—Robert A. Wax
*Assistant Examiner*—Tekchand Saidha
*Attorney, Agent, or Firm*—Richard Aron Osman

[57] ABSTRACT

The kinase suppressor of Ras (Ksr), a novel protein kinase involved in the regulation of cell growth and differentiation, provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease. The invention includes methods, including phosphorylation and binding assays, for screening chemical libraries for lead compounds for a pharmacological agent useful in the diagnosis or treatment of disease associated Ksr activity or Ksr-dependent signal transduction.

6 Claims, No Drawings

PROTEIN KINASE REQUIRED FOR RAS SIGNAL TRANSDUCTION

This is a division of application Ser. No.08/571,758 filed Dec. 13, 1995, now U.S. Pat. No. 5,700,675.

The research carried out in the subject application was supported in part by grants from the National Institutes of Health. The government may have rights in any patent issuing on this application.

INTRODUCTION

1. Field of the Invention

The field of the invention is a protein kinase required for Ras signal transduction and its use in pharmaceutical screens.

2. Background

Ras plays a crucial role in diverse cellular processes, such as proliferation and differentiation, where it functions as a nodal point transmitting signals originating from receptor tyrosine kinases (RTKs) to a variety of effector molecules (reviewed in McCormick, 1994a; van der Geer et al., 1994; Burgering and Bos, 1995). Ras activation, which involves a switch from an inactive GDP-bound to an active GTP-bound state, is promoted by a guanine nucleotide-exchange factor. Upon RTK activation, the exchange factor is recruited by an SH2/SH3 domain-containing adaptor molecule to the RTK at the plasma membrane where it can contact and activate Ras. GTP-bound Ras then transmits the signal to downstream effector molecules.

The protein serine/threonine kinase Raf has been identified as a major effector of Ras (reviewed in Daum et al., 1994; McCormick, 1994b). Upon Ras activation, Raf is recruited to the plasma membrane by a direct interaction with Ras, where it is subsequently activated by an unknown mechanism. Raf activation initiates an evolutionarily conserved pathway involving two other kinases, MEK (MAPK Kinase) and MAPK (Mitogen-Activated Protein Kinase) that convey signals to the nucleus through a directional series of activating phosphorylations (reviewed in Marshall 1994). Although this model for Ras-dependent signal transduction is well-supported, there are still major issues that remain poorly understood. One of them is the mechanism by which Raf is activated. Recent evidence suggests that once recruited to the plasma membrane Raf is activated by phosphorylation (Dent and Sturgill, 1994; Dent et al., 1995). However, a candidate kinase(s) has yet to be identified. Another unresolved issue is the nature of other Ras effectors as well as the pathways they control. Although Raf is clearly a major Ras target, it can not account for all of the cellular responses mediated by Ras (for example see White et al., 1995).

Ectopic expression of an activated Ras1 allele, Ras1$^{V12}$, in the developing Drosophila eye transforms non-neuronal cone cells into R7 photoreceptor cells (Fortini et al., 1992). Similar results are obtained by expression of an activated Drosophila Raf allele, D-Raf$^{Tor4021}$ (Dickson et al., 1992). We carried out a genetic screen designed to isolate mutations that modify the signaling efficiency of Ras1$^{V12}$. Most mutations that decreased the signaling efficiency of Ras1$^{V12}$ also decreased the efficiency of D-Raf$^{Torso4021}$ signaling. However, two groups of mutations were identified that did not alter D-Raf$^{Torso4021}$ signaling. We disclose here the characterization of their respective loci. The Suppressor of Ras1 2—2 (SR2-2) locus encodes a protein homologous to the catalytic subunit of the prenylation enzyme type I geranylgeranyl transferase. We have renamed this locus βGGT-I. The second locus, SR3-1, encodes a novel protein kinase distantly related to Raf kinase members. Based on its sequence and the ability of mutants to reduce Ras1-mediated signaling, we renamed this locus kinase suppressor of ras (ksr). In addition to its function in the Sevenless RTK pathway, we show that ksr is also required for signaling by the Torso RTK We have isolated mouse and human homologs of ksr. Together, these data indicate that Ksr is an evolutionarily conserved component of the Ras signaling pathway. As such, the human Ksr provides an important target for pharmaceutical intervention.

Relevant Literature

Recent reports on Raf activation include Dent and Sturgill 1994; Dent et al., 1995; White et al., 1995, Yao et al, 1995; and a recent review by Marshall, 1994.

SUMMARY OF THE INVENTION

The invention provides methods and compositions relating to a novel protein kinase involved in the regulation of cell growth and differentiation: kinase suppressor of Ras (Ksr). As such, the kinase provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease.

The invention includes methods for screening chemical libraries for lead compounds for a pharmacological agent useful in the diagnosis or treatment of disease-associated Ksr activity or Ksr-dependent signal transduction. In one embodiment, the methods involve (1) forming a mixture comprising a Ksr, a natural intracellular Ksr substrate or binding target such as the 14-3-3 gene product, and a candidate pharmacological agent; (2) incubating the mixture under conditions whereby, but for the presence of said candidate pharmacological agent, said Ksr selectively phosphorylates said substrate or binds said binding target at a control rate; and (3) detecting the presence or absence of a change in the specific phosphorylation of said substrate by said Ksr or phosphorylation or binding of said Ksr to said binding target, wherein such a change indicates that said candidate pharmacological agent is a lead compound for a pharmacological agent capable of modulating Ksr function.

DETAILED DESCRIPTION OF THE INVENTION

A Drosophila melanogaster, a Drosophila virilis, a murine and a human ksr encoding sequence are set out in SEQ ID NO: 1, 3, 5 and 7, respectively. A Drosophila melanogaster, a Drosophila virilis, a murine and a human ksr protein sequence are set out in SEQ ID NO: 2, 4, 6 and 8, respectively. Ksr proteins necessarily include a disclosed ksr kinase domain. Hence, Ksr proteins include deletion mutants of natural ksr proteins retaining the ksr kinase domain.

Natural nucleic acids encoding ksr proteins are readily isolated from cDNA libraries with PCR primers and hybridization probes containing portions of the nucleic acid sequence of SEQ ID NO: 1, 3, 5 and 7. Preferred ksr nucleic acids are capable of hybridizing with one of these sequences under low stringency conditions defined by a hybridization buffer consisting essentially of 1% Bovine Serum Albumin (BSA); 500 mM sodium phosphate (NaPO$_4$); 1 mM EDTA; 7% SDS at a temperature of 42° C. and a wash buffer consisting essentially of 2X SSC (600 mM NaCl; 60 mM Na Citrate); 0.1% SDS at 50° C.; more preferably under low stringency conditions defined by a hybridization buffer consisting essentially of 1% Bovine Serum Albumin (BSA); 500 mM sodium phosphate (NaPO4); 15% formamide; 1 mM EDTA; 7% SDS at a temperature of 50° C. and a wash buffer consisting essentially of 1X SSC (300 mM NaCl; 30 mM Na Citrate); 0.1% SDS at 50° C.; most preferably under low stringency conditions defined by a hybridization buffer consisting essentially of 1% Bovine Serum Albumin (BSA); 200 mM sodium phosphate (NaPO4); 15% formamide; 1 mM EDTA; 7% SDS at a temperature of 50° C. and a wash buffer consisting essentially of 0.5X SSC (150 mM NaCl; 15 mM Na Citrate); 0.1% SDS at 65° C.

The subject nucleic acids are recombinant, meaning they comprise a sequence joined to a nucleotide other than that to which sequence is naturally joined and isolated from a natural environment. The nucleic acids may be part of Ksr-expression vectors and may be incorporated into cells for expression and screening, transgenic animals for functional studies (e.g. the efficacy of candidate drugs for disease associated with expression of a Ksr), etc. These nucleic acids find a wide variety of applications including use as templates for transcription, hybridization probes, PCR primers, therapeutic nucleic acids, etc.; use in detecting the presence of Ksr genes and gene transcripts, in detecting or amplifying nucleic acids encoding additional Ksr homologs and structural analogs, and in gene therapy applications, e.g. using antisense nucleic acids or ribozymes comprising the disclosed Ksr sequences or their complements or reverse complements.

The invention also provides Ksr-specific binding reagents such as antibodies. Such reagents find a wide variety of application in biomedical research and diagnostics. For example, antibodies specific for mutant Ksr allele-products are used to identify mutant phenotypes associated with pathogenesis. Methods for making allele-specific antibodies are known in the art. For example, an mKsr-specific antibody was generated by immunizing mice with a unique N-terminal mKsr peptide (residues 118–249) GST fusion.

The invention provides efficient methods of identifying pharmacological agents or lead compounds for agents active at the level of a Ksr modulatable cellular function, particularly Ksr mediated signal transduction. For example, we have found that a binding complex comprising Ksr, 14-3-3 and Raf exists in stimulated cells; modulators of the stability of this complex effect signal transduction. Generally, the screening methods involve assaying for compounds which interfere with a Ksr activity such as kinase activity or target binding. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising Ksr and one or more natural Ksr intracellular binding targets including substrates or otherwise modulating Ksr kinase activity. Target indications may include infection, genetic disease, cell growth and regulatory or immunologic dysfunction, such as neoplasia, inflammation, hypersensitivity, etc.

A wide variety of assays for binding agents are provided including labeled in vitro kinase assays, protein-protein binding assays, immunoassays, cell based assays, etc. The Ksr compositions used in the methods are recombinantly produced from nucleic acids having the disclosed Ksr nucleotide sequences. The Ksr may be part of a fusion product with another peptide or polypeptide, e.g. a polypeptide that is capable of providing or enhancing protein-protein binding, stability under assay conditions (e.g. a tag for detection or anchoring), etc.

The assay mixtures comprise one or more natural intracellular Ksr binding targets including substrates, such as the 14-3-3 gene product, or, in the case of an autophosphorylation assay, the Ksr itself can function as the binding target. A Ksr-derived pseudosubstrate may be used or modified (e.g. A to S/T substitutions) to generate effective substrates for use in the subject kinase assays as can synthetic peptides or other protein substrates. Generally, Ksr-specificity of the binding agent is shown by kinase activity (i.e. the agent demonstrates activity of an Ksr substrate, agonist, antagonist, etc.) or binding equilibrium constants (usually at least about $10^6 M^{-1}$, preferably at least about $10^8 M^{-1}$, more preferably at least about $10^9 M^{-1}$). A wide variety of cell-based and cell-free assays may be used to demonstrate Ksr-specific binding; preferred are rapid in vitro, cell-free assays such as mediating or inhibiting Ksr-protein binding, phosphorylation assays, immunoassays, etc.

The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

In a preferred in vitro, binding assay, a mixture of a protein comprising at least one of the conserved Ksr domains, including CA1, CA2, CA3, CA4 and the kinase domain (see Table 1), one or more binding targets or substrates and the candidate agent is incubated under conditions whereby, but for the presence of the candidate pharmacological agent, the Ksr specifically binds the cellular binding target at a first binding affinity or phosphorylates the substrate at a first rate. After incubation, a second binding affinity or rate is detected. Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected.

The following experiments and examples are offered by way of illustration and not by way of limitation.

EXPERIMENTAL

Mutations in the SR2-2 and SR3-1 loci suppress the eye phenotype of activated Ras1 but not that of activated D-Raf.

Ectopic expression of activated Ras1 (Ras1$^{V12}$) under control of sevenless (sev) promoter/enhancer sequences (sev-Ras1$^{V12}$) transforms cone cells into R7 photoreceptor cells (Fortini et al., 1992). These extra R7 cells disorganize the ommatidial array, which causes a roughening of the external eye surface. The severity of eye roughness appears proportional to the strength of $Ras1^{V12}$-mediated signaling since two copies of the transgene produce a much more disrupted eye than one copy. We took advantage of this sensitized system to conduct a screen for mutations that reduce (suppressors) or increase (enhancers) the degree of eye roughness. We reasoned that a two-fold reduction in the dose of a gene (by mutating one of its two copies) that functions downstream of Ras1 should dominantly alter signaling strength which in turn should visibly modify the roughness of the eye. Based on this assumption, we screened ~200,000 EMS- and ~650,000 X-ray-mutagenized progeny for dominant modifiers of the $Ras1^{V12}$-mediated rough eye phenotype. 18 complementation groups of suppressors with multiple alleles and 13 complementation groups of enhancers of sev-$Ras1^{V12}$ were isolated.

To characterize further the various groups of suppressors, we tested their ability to suppress dominantly the extra R7 cell phenotype caused by overexpression of an activated Drosophila Raf allele (sE-$Raf^{Tor4021}$). Since Raf functions directly downstream of Ras, we expected most of our suppressor groups to modify similarly the sE-$Raf^{Tor4021}$ phenotype. Interestingly, two recessive lethal suppressor groups, SR2-2 and SR3-1 did not reduce the number of extra R7 cells produced by D-$Raf^{Tor4021}$ expression. Scanning electron micrographs of adult eyes illustrate the suppressor phenotypes of one SR3-1 allele. Similar results were obtained with multiple SR2-2 and SR3-1 alleles. We also monitored the suppression of extra R7 cells by counting the number of R7 photoreceptors in cross-sections of adult fly retinae. In wild-type there is one R7 cell per ommatidium, whereas in sev-$Ras1^{V12}$/+ flies we observed 2.3 (n=437) R7 cells per ommatidium. This number was reduced to 1.2 (n=481) R7 cells per ommatidium in sev-$Ras1^{V12}$/+; SR3-$1^{S-638}$/+ flies. In sE-$Raf^{Tor4021}$ /+ flies, 2.3 (n=302) R7 cells per ommatidium were observed. However, this number remained at 2.3 (n=474) in sE-$Raf^{Tor4021}$/+; SR3-$1^{S-638}$/+ flies reflecting the inability of SR3-1 mutations to alter sE-$Raf^{Tor4021}$ signaling strength.

Targeting of $Ras1^{V12}$ to the plasma membrane by myristylation distinguishes SR2-2 from SR3-1.

Prenylation of the C-terminal CAAX box (C=cysteine, A=aliphatic residue, X=any amino acid) is the major post-translational modification specific to all Ras-like GTPases. When the residue at position "X" is a leucine, as in Ras1, a geranylgeranyl group is added by a type I geranylgeranyl transferase. The addition of this lipidic moiety is required to attach Ras to the plasma membrane (reviewed in Glomset and Farnsworth, 1994). Deletion of the CAAX box abolishes Ras function (Willumsen et al., 1984; Kato et al., 1992), however its activity can be restored if it is brought to the membrane by another localization signal, such as a myristyl group (Buss et al., 1989).

One possibility to account for the ability of a mutant to suppress sev-$Ras1^{V12}$ but not sE-$Raf^{Tor4021}$ is that the locus encodes an enzyme that is required for the membrane localization of Ras1. Consequently, mutations in this locus would not affect D-$Raf^{Tor4021}$. To directly test this possibility, we asked if SR2-2 or SR3-1 alleles could suppress activated Ras1 if it is targeted to the membrane by an alternative mechanism. We targeted $Ras1^{V12}$ to the membrane by fusing the first 90 amino acids of Drosophila Src kinase (D-Src; Simon et al., 1985), which contains a myristylation signal, to $Ras1^{V12}$ deleted of its CAAX box (sev-Src90$Ras1^{V12\Delta CAAX}$). While the CAAX box-deleted $Ras1^{V12}$ is inactive, Src90Ras1 produces the same phenotype as $Ras1^{V12}$; that is, it generates extra R7 cells and disrupts the ommatidial array.

We crossed sev-Src90$Ras1^{V12\Delta CAAX}$ flies to SR2-2 and SR3-1 alleles and analyzed the rough eye phenotype. SR2-$2^{S-2110}$ did not suppress the rough eye phenotype while SR3-$1^{S-638}$ suppressed the rough eye phenotype and the production of extra R7 cells. These observations indicate that SR2-2 is involved in prenylation of Ras1 while SR3-1 encodes a component of the Ras1 pathway that is not involved in the process of Ras1 membrane localization.

The SR2-2 locus encodes the Drosophila homolog of the β-subunit of type I geranylgeranyl transferase.

The SR2-2 locus was meiotically mapped to 2-15 (cytological position 25B-C), based on the ability of different mutant alleles to suppress sev-$Ras1^{V12}$. One of the seven recessive lethal SR2-2 alleles recovered contains an X-ray-induced inversion (SR2-$2^{S-2126}$) with a breakpoint at 25B4-6. Genomic DNA spanning this breakpoint was isolated and used to screen a Drosophila eye-antennal imaginal disc cDNA library (see Experimental Procedures). A single class of cDNAs (ranging in size from 0.8 to 1.6 kb) defining a transcription unit disrupted by the inversion present in SR2-$2^{S-2126}$, was identified and characterized. Conceptual translation of the longest open reading frame (ORF) defined by these cDNAs predicts a protein of 395 amino acids. Determination of the gene structure by sequencing the corresponding genomic region revealed four exons with the first in-frame methionine located at the beginning of the second exon. The SR2-$2^{S-2126}$ inversion breakpoint maps to the 5'-end of the transcript. Further confirmation that this ORF corresponds to the SR2-2 gene, was provided by sequence analysis of two other mutant alleles, SR2-$2^{S-483}$ and SR2-$2^{S-2554}$, both of which have small deletions that remove the first exon and part of the 5' regulatory sequences. A search of the current protein databases with this ORF indicated that the SR2-2 gene encodes the Drosophila homolog of the catalytic β-subunit of type I geranylgeranyl transferase (BGGT-I) (Marshall, 1993). Sequence alignment with the human and the yeast S. pombe βGGT-I proteins shows a high degree of evolutionary conservation. The human sequence is 44% identical (69% similar) to the Drosophila sequence throughout the entire ORF while the yeast sequence is 36% identical (57% similar) to the Drosophila protein. We therefore renamed this locus, βGGT-I.

The SR3-1 locus encodes a novel protein kinase.

The ability of SR3-1 mutant alleles to suppress the sev-$Ras1^{V12}$ phenotype was meiotically mapped to 3-47.5, which corresponds to a region near the chromocenter of the third chromosome. The map position was further refined by showing that SR3-1 meiotically maps between two P-elements inserted at 82F8-10 and 83A5-6, respectively. X-ray-induced chromosomal deletions were generated by selecting w⁻ revertants of one of the P-element insertions. One such deletion, Df(3R)e1025-14, which removes the chromosomal region from 82F8-10 to 83A1-3, complemented the SR3-1-associated lethality. Taken together, these results indicated that the SR3-1 locus lies between 83A1-3, the distal breakpoint of Df(3R)e1025-14, and 83A5-6, the insertion site of P[w⁺]5E2.

Five overlapping cosmids which cover this chromosomal region were recovered by chromosome walking. To identify restriction site polymorphisms that might have been induced in the SR3-1 alleles, these cosmids were used to probe genomic DNA blots prepared from 9 independent X-ray-induced SR3-1 alleles. Cosmid III revealed polymorphisms in a BamHI restriction digest of two alleles, SR3-$1^{S-69}$ and SR3-$1^{S-511}$. No other cosmid revealed polymorphisms in the 9 tested alleles. A 7 kb SacII genomic fragment which spans the polymorphic BamHI fragments was introduced into the germline by P-element-mediated transformation. This genomic fragment, tested in transgenic flies, rescued both the lethality and the sev-Ras1$^{V12}$-suppression ability of three independent SR3-1 alleles. A single class of cDNAs that was totally encoded by the 7kb genomic fragment was identified by screening a Drosophila eye-antennal imaginal disc cDNA library and sequenced. The longest cDNA clone represents a transcript of 3.6 kb which is close to the size of a full-length transcript since RNA blot analysis identified a single band of similar size. Sequence analysis of the genomic region revealed that this transcript is encoded by a single exon. Conceptual translation of the longest ORF predicts a protein of 966 amino acids. The presence of an in-frame stop codon upstream of the predicted initiating methionine indicates that this cDNA contains the complete ORF.

A search of current protein databases indicated that SR3-1 encodes a novel protein kinase. The putative catalytic domain, which is C-terminal, contains the characteristic eleven conserved sub-domains found in eukaryotic kinases (Hardie and Hanks, 1995) and is preceded by a long N-terminal region with three distinctive features: a cysteine-rich domain similar to those found in Protein Kinase C isozymes (Hubbard et al., 1991) and Raf kinases (Bruder et al., 1992); four sequences that match the consensus phosphorylation site (PXS/TP) for MAPK (Marshall 1994); and a block of amino acids rich in serines and threonines followed by a conserved motif (FXFPXXS/T) that resembles the sequence around the Conserved Region 2 (CR2) domain of Raf kinases (Heidecker et al., 1992). Since the SR3-1 locus encodes a putative protein kinase and mutant alleles were isolated as suppressors of sev-Ras1$^{V12}$, we renamed this locus kinase suppressor of ras (ksr).

Further confirmation that this gene corresponds to the ksr (SR3-1) locus was provided by sequencing three ksr alleles which revealed mutations disrupting the Ksr ORF (Table 1).

TABLE 1

Sequence comparison of the Ksr kinases.

```
                                                                                          as (S-548)
                                                      CA1                                      ▼
Dm Ksr   . m s s N N N a . . . . . p A s A P d T g s T . . n A n D P I S G s L S V D s n l V i|i q d m i d l s a n h l e g l r t q c a l s S t l t q q e i r c l e s k l v r y| 112
Dv Ksr   . m s s S A A a Q L T A P P v N s N S N S s S . . . n N n T T T T A s . . E s n l l i|i q d m i d l s a n h l e g l r t q c a T s A t l t q q e i r c l e s k l v r y| 116
mKsr-1   M D R A A L R a A A M G E K K E G G G g A A . . A D G G A G A A V S R A L Q Q C G Q L|q K L i d l S I G S l R g l r t t K c S V s N D l t q q e i r T l e A k l v K y| 115
hKsr-1   R A A L R S A A L G E K K E G G C C g D A A I A E G G A G A A A S R T L Q Q C G Q L|q K L i d l S I G S L R g l r t t K c V V s N D l t q q e i r T L e A k l v R y| 117 f s e l l l A k M r l n e r i p a n g l V p h . . T t g n e l r q w l r v v g          112
Dm Ksr   l s Q G T l T a c l a r l t t l e q s l R l s d e e l R q l l a D S P s Q R e c e e e l r r l t R a m Q n l r k c m e s l E s G t a . . a s n N d p e q w h w d s w d r . 229
Dv Ksr   l s P E S l N a c l a r l t t l e q T l Q l s d e e l K q l l a H N S s T Q L D e e l r r l t K a m H n l r k c m e T l D s S G a V a s n V d p e q w h w d s w d r P 235
mKsr-1   V R P E V V Q E I P Q E l . t l D A L l E M D E A K A K E M I R R W G A S T e c C S . . . . . R l Q Q A L T C l R K V t G L G G E H K M D S G W S S T D A r D 213
hKsr-1   V R P E V V Q E I P R D l . t l D A L l E M N E A K V K E T l R R C G A S G D e C G . . . . . R l Q Y A L T C L R K V t G L G G E H K E D S W S S L D A r R 226

. p T h l h r g s V g n . . . . . . . . . . . . . . i g l g N n s t a s p r T h h r q h G V K G K n s  229
                                                          H p H h M h r g s I g n . . . . . . . . . . . . . . i g l g . L s S a s p r A h h r q h Q H Q H A n s  235
                                                          S S L G P P M D M L S S . . . . . . . . . . . . . . . . . . . . . . L g R A G A s t Q G p r S . . . . 213
                                                          E S G S G P S T D T L S A S L P W P P G S S Q L R A G n s A Q G p r S . . . . . . . . . . . . . . . . 226
                                                                                                                                        CA2
                                                                                                                    ┌─────────────────────────────────────────┐
                                                                                                                    │ . g t p p p a r k h q t l l . . . . . . . │
                                                                                                                    │ . g t p p p a K k h q t l l . . . . . . . │
                                                                                                                    │ H A K L K P P R t P p p p S r k V F Q l l . │
                                                                                                                    │ H T K L K P P R t P p p p S r k V F Q l l M H N S│
                                                                                                                    └─────────────────────────────────────────┘

Dm Ksr   A L A N S T n F K s G R Q s P S A T E e L N S T Q g s q l t l t l t p s p p n s p f t p s s g L S s . . S L N g t p q r s r . . . . . . . . . . . . . . . . . . . . . . . 336
Dv Ksr   K P K I V N n S A s s S R s . . . e Q Q P L T g s q l t l t l t p s p p n s p f t p A s g T A s A . S g t P q r s r S T T T A A . . . . . . . . . . . . . . . . . . . . . 349
mKsr-1   . . . I S V S A L P A S D S P V P G L S E G L S D s C I P l H T S . . G R L T p R A L H s F I T P P T T Q L R r H A K L K P P R t P p p p S r k V F Q l l . . . . . . . . . 306
hKsr-1   . . . I S V S A L P A S D S P T P S F S E G L S D T C I P l H A S . . G R L T p R A L H s F I T P P T T Q L R r H T K L K P P R t P p p p S r k V F Q l l M H N S . . . . . 319

. s Q S H V Q V D G E Q L A r N r l p t d p s T d s h s s T . s s d i f   336
                                                                          S A s E T A L A E Q P P R P P r S r l p t d p s P d s h s s A S s s d i f   349
                                                                          . . . . . . . . . . . . . . . . . . P S F p t L T R S K s h E s Q L G N R i   306
                                                                          . . . . . . . . . . . . . . . . . . P S F p t L T R S K s h E s Q L G N R i   319
                                                                                                                        CA3
                                                                                                            ┌──────────────────────────────────────────────────────────────┐
                                                                      ● ● ● ● ●                             │ ● ● ● ● ● ● ● ●                              ● ● ● ● ● ●    │
Dm Ksr   v d P N T N A S S G G s s s n v l M v|p C s p g v G h v g m g h A|i k h r f T k A L g f m a t . . c T l c q k q V f H R w M k c t d c k y i c h k s c a p h v p p s q g 
Dv Ksr   v d . . . . . . G G S I N s s n v l L v p P s p g v A h v g m g h T|t k h r f S k W F g f m a t . . c K l c q k q M M S H w F k c t d c k y i c h k s c a p h v p p s q g 
mKsr-1   . . D D V T P M K F E L P H G s p Q L V R R D I g L s|V T h r f D T K S W L S Q V . c H V c q k S M I F G . V k c K H c R L K c h N K c T K E . A p A q R 310
hKsr-1   . . D D V s s M R F D L S H G s p Q M V R R D I g L s|V T h r f D T K S W L S Q v . c H V c q k S M I F G . V k c K H c R L K c h N K c T K E . A p A q R 
D-Raf    263 i k h Q I I R K T F f S L V F c E G c R R L L f T G F . Y c S Q c N F R F h Q R c a N R v p M L c q R 
hc-Raf   136 T T h N f A R K T F L K L A F c D I c q k F L L N G F R R c c D I c q k F h E H c S T K v p T M d 184
```

TABLE 1-continued

Sequence comparison of the Ksr kinases.

```
DmKsr  lpreyvDefrHIKEQgGYASLpHVhGaAkGspLVKks      455
DvKsr  lpreyvHefrQTQVGgRWD..pAQhSSSkASpVPRks      461
mKsr-1 ITFLPLARLrRTESVPSDINNpVDRAaEPHEGTLPkA      415
hKsr-1 ISFLPLTRLrRTESVPSDINNpVDRSaEPHFGTLPkA      428
                                    CA4

DmKsr  .sGGsGgVSlisnepVPEQFPtAPaTangGLD.          558
DvKsr  .sGGsGgVSlisnepQAHMATtESTLTngNNNSS         578
mKsr-1 NACNsNAsAAQTlisnepQAHMATtESTLTngNNNSS      578
              AAPLsSTADsTRl.DDQpKTDVLGVHEaEaEEPEAGK      517
              AAPLPEAADgTRl.DDQpKADVLEAHEaEaEEPEAGK      543

DmKsr       seCtdthksndsdktvslsgsastdsdrtpvrVdste    655
DvKsr       seYtdthksndsdktvslsgsastdsdrtpvrLdste    692
mKsr-1      G.................sffprklsNagvdkrVpft    547
hKsr-1      G.................PIsRKas............    572
                          T (S-638)        T (S-721)
                          ▲                ▽
                                           III DmKsr  dgdsqqwrqnsislkewdipygdlllleriggggrfgtvhralwhgdvavklInedylgdehmleTfrSevanfkNtrhenlvl  775
DvKsr  dgdsgqwrqnsislkewdipygdlHllerigggqrfgtvhralwhgdvavklInedylgdehmleSfrNevanfkKtrhenlvl  812
mKsr-1 .........qTsVYlQewdiPFEQVElGePigqgrWgRvhrGRwhgEvaIRl1EMdGHNQDh.1KLfKKevMnYRQtrhenVvl  658
hKsr-1 .........qTsVYlQewdiPFEQVElGePigqgrWgRvhrGRwhgEvaIRl1EMdGHNQDh.1KLfKKevMnYRQtrhenVvl  683
D-Ral       DAKSsEENwNiLAEEIIiGPrigSgSfgtvYraHwhgPvPvkTInvKTPSPAQ.1QAfKNevaMLKktrhCnILl         565
hc-Ral      GQRDsSYYwEiEASEVMlSTriggSgSfgtvYKCKwhgdvavkIlKVVDPTPeQ.FQAfrNevaVLRKtrhVnIL1         443
                                          I                            II DmKsr  fmgacmnppylaivtslckgntlytyihqrrekfamn     775
DvKsr  fmgacmnppylaivtAlckgntlytyihqrrekfamn     812
mKsr-1 fmgacmnppHlaiItsFckgRtlHSFVRDPKTSLDIn     658
hKsr-1 fmgacmnppHlaiItsFckgRtlHSFVRDPKTSLDIn     683
D-Ral  fmg.cVSKpslaivtQWcEgSSlyKHVhVSETkfKLn     565
hc-Ral fmg.YmTKDNlaivtQWcEgSSlyKHLhVQETkfQmF     443
                                         IV
                                          V
```

TABLE 1-continued

Sequence comparison of the Ksr kinases.

```
Dm Ksr   r t l l i a q q i a q g m g y l h a r E i i h k d l r t k n i f i e n g . k v i i t d f g l f s s t k l l y c d m . . . g l g v p h n w l c y l a p e l i r a l q p E
Dv Ksr   r t l l i a q q i a q g m g y l h a r D i i h k d l r t k n i f i e n g . k v i i t d f g l f s s t k l l y c d m . . . g l g v p Q n w l c y l a p e l i r a l q p C
mKsr-1   K t R Q i a q E i I K g m g y l h a K G i V h k d l K S k n V f Y D n g . k v V i t d f g l f G I S G V V R E E R R E N Q l K L S h D w l c y l a p e I V r E M I p G
hKsr-1   K t R Q i a q E i I K g m g y l h a K G i V h k d l K S k n V f Y D n g . k v V i t d f g l f G I S G V V R E G R R E N Q l K L S h D w l c y l a p e I V r E M T p G
D-Ral    T L I D i G R q V a q g m D y l h a K N i i h R d l K S N n i f L H E D L S v K i G d f g l A T A K T R W S G E K Q A N Q . . p T G S I L W M a p e V i r . . . . . .
hc-Ral   Q L I D i a R q T a q g m D y l h a K N i i h R d M K S N n i f L H E g L T v K i G d f g l A T V K S R W S G S Q Q V E Q . . . p T G S V L W M a p e V i r . . . . . .
                                      VIb                                                                      VII                      VIII
```

```
Dm Ksr    k p R g e c l e f t P y s d v y s f g t v w y e l i c g e f t f k d q p a  891
Dv Ksr    k p P g e c l e f t S y s d v y s f g t v w y e l i c g e f t f k d q p a  928
mKsr-1    R D E D Q . l P f S K A A d v y A f g t v w y e l Q A R D W P f k H q p a   776
hKsr-1    k D E D Q . l P f S K A A d v y A f g t v w y e l Q A R D W P L k N q A a  801
D-Ral     . . M Q e L N P Y S F Q s d v y A f g I v M y e l L A E C L P Y G H I S N   575
hc-Ral    . . M Q D N N P f S F Q s d v y S Y g I v L y e l M T g e L P Y S H I N N   553
                                                          IX
```

```
Dm Ksr    . e s i i w q v g r . . g m k q s l a n l q s g . . . r d v k d l l m l c w t y e k e h r p Q f a r l l s l l e h . . . . . . . l p k k r l a r s p s h p v n l s r s a e s v f
Dv Ksr    . e s i i w q v g r . . g m k q s l a n l q s g . . . r d v k d l l m l c w t y e k e h r p D f a r l l s l l e h . . . . . . . l p k k r l a r s p s h p v n l s r s a e s v f
mKsr-1    . e A L i w q I g S G E g V R R V l a S V S L g . . . K E v G E I I S A c w A F D L Q E r p s f S L F M D M l e R . . . . . . l p k . . l N r R L s h p G H F W K s a D I N S
hKsr-1    . e A S i w q I g S G E g m k R V l T S V S L g . . . K E v S E I I S A c w A F D L Q E r p s f S L F M D M l e K . . . . . . l p k . . l N r R L s h p G H F W K s a e L
D-Ral     K D Q i L F M v g r G L . L R P D M S Q V R s D A R r H S k R l A E D c I K y T P K D r p L f R P l l W M l e N M L R T l p k . . I H r s A s E p . n l T Q s Q L Q N D
hc-Ral    R D Q i i F M v g r G Y . A S P D I S K l Y K N C P K A M k R l V A D c V K K V k e E r p L f P Q I l s S I e L L Q H S l p k . . I N r s A s E p . S l H r A a H T E D
            X                                                                                                 XI
```

```
Dm Ksr                                                                                                                                              966
Dv Ksr                                                                                                                                             1003
mKsr-1    (SEQ ID NO:2)                                                                                                                              973
hKsr-1    (SEQ ID NO:4)                                                                                                                              874
D-Ral     S K V M P F F E R F G L G T L E S G N P K M (SEQ ID NO:6)                                                                                   791
hc-Ral    (SEQ ID NO:8)                                                                                                                              648
          . . E F L Y L P S P K T P V N F N N F G F F G S A G N N (SEQ ID NO:11)
          I N A C T L T T S P R L P V F (SEQ ID NO:12)
```

Table 1 provides a detailed comparison of the predicted amino acid sequence of Ksr kinases. Conceptual translation of the open reading frame from the longest D. melanogaster (Dm) Ksr cDNA is shown. The positions of mutations in three ksr alleles are indicated: S-548 is a 4 bp X-ray-induced mutation affecting two consecutive codons (CTG-CGA to AGT-GGA). S-638 is an EMS-induced allele that has two separate point mutations changing a GCC codon to GTC and GCG codon to ACG. S-721 is a frameshift mutation due to a 10 bp duplication from adjacent sequences within the codon for asparagine-727. Also shown in the alignment are the conceptual translations of the open reading frames for the Ksr genes from other species: the D. virilis (Dv) Ksr sequence was derived from genomic DNA, the mouse (m) Ksr-1 from a 4 kb cDNA, and the human (h) Ksr-1, deduced from three overlapping cDNA clones (the N-terminal two residues were absent from these clones so the numbering begins with the third residue). The human Ksr is present as one or more of a plurality of alternatively spliced forms, exemplified by Ksr' in the following sequence listing. The amino acid sequences (and their respective positions) for the cysteine-rich regions and the kinase domains of Drosophila (D-Raf) and human (h c-Raf) (Genbank accession number: X07181 and X03484, respectively) are presented. Residues identical to Dm Ksr are lower case. In the N-terminus of the Ksr kinases four Conserved Areas (CA1 to CA4) are boxed. CA1 is a novel domain present only in the Ksr kinases. CA2 is a proline-rich stretch that may represent an SH3-binding site (Alexandropoulos et al., 1995). CA3 is a cysteine-rich stretch, simlar to a domain found in multiple signaling molecules. This conserved sequence is also part of the CR1 domain found in Raf kinases (Bruder et al., 1992). CA4 is a long serine/threonine-rich stretch followed by a conserved motif (indicated by a dashed line). This domain resembles the region around the CR2 domain of Raf kinases (Heidecker et al., 1992). The four short thick lines overlying the sequences indicate potential sites of phosphorylation by MAPK (PXS/TP) found in Dm Ksr. The eleven conserved sub-domains characteristic of protein kinases are indicated by roman numerals below their approximate positions.

ksr$^{S-638}$ has two single amino acids changes: alanine-696 to valine and alanine-703 to threonine. The latter substitution alters a highly conserved residue within kinase sub-domain II (Hanks et al., 1988). ksr$^{S-721}$ contains a 10 bp insertion in the codon for asparagine-727 within kinase sub-domain III creating a frameshift mutation that truncates the protein at kinase sub-domain III. ksr$^{S-548}$ has a four base pair substitution that changes two consecutive amino acids in the N-terminus of the protein: leucine-50 and arginine-51 to glycine and serine, respectively. Unlike the 16 alleles recovered in the screen which were recessive lethal, ksr$^{S-548}$ produces sub-viable flies which have rough eyes (see below), indicating that it is a weak loss-of-function mutation.

Identification of Ksr homologs in other species defines a novel class of kinases related to Raf kinases.

As a first attempt to determine functionally important domains that comprise the Ksr kinase, we searched for homologs from other species. First, we isolated the complete coding region of ksr from a Drosophila virilis genomic library by low-stringency hybridization (see Experimental Procedures). The D. virilis genomic sequence revealed a single uninterrupted ORF predicting a protein of 1003 amino acids (Table 1). The D. virilis and D. melanogaster Ksr proteins are 96% identical within the kinase domain while the N-terminal region is more divergent (69% identity), although islands of high conservation are present (see Table 1).

A search of translated nucleotide databases (using the TBLASTN program; Altschul et al., 1990) identified a partial ORF derived from a mouse DNA sequence with significant blocks of similarity to the N-terminus of Ksr. This sequence, named hb, had been isolated by Nehls et al. (1994) as part of an exon-trapping strategy to establish the transcription map of a 1 Mb region around the mouse NF1 locus. To determine if the full-length hb transcript also contains a kinase domain related to Ksr, we screened a cDNA library derived from a mouse PCC4 teratocarcinoma cell line with a probe corresponding to the hb sequence (see Experimental Procedures). A 4 kb cDNA clone was isolated and encodes a protein of 873 amino acids that contains a kinase domain highly related to the Ksr kinase domain (51% identity/74% similarity; Table 1). In addition, a human fetal brain cDNA library was screened at low-stringency with the same hb probe (see Experimental Procedures). Thirteen independent cDNA clones were purified and sequenced. They represent partial transcripts ranging in size from 0.6 to 3 kb. Interestingly, they define at least three classes of N-terminal splicing variants. The predicted protein sequence derived from overlapping human cDNA clones is shown in Table 1. With the exception of the first divergent 23 amino acids, which probably represents an alternative exon, human Ksr-1 (hKsr-1) is nearly identical to mouse Ksr-1 (mKsr-1; 95% identity/99% similarity). Subsequent to this analysis, two human Expressed Sequence Tags (GenBank accession numbers: R27352 and R27353) have been reported that correspond to regions of the hKsr kinase domain.

Comparison of mammalian and Drosophila Ksr sequences showed similarity throughout the kinase domain as well as at various locations within the N-terminal region (Table 1). Sequence conservation is obvious within all sub-domains of the kinase domain. Two interesting features are present within sub-domains VIb and VIII. HRDL(K/R/A)XXN (D and N are invariant residues) is the consensus sequence corresponding to sub-domain VIb for the majority of known kinases (Hardie and Hanks, 1995). Instead of an arginine at the second position, a lysine is present for the Ksr homologs which distinguishes them from most other kinases. In addition, the amino acids N-terminal to the APE motif in sub-domain VIII, which have been implicated in substrate recognition specificity, (Hardie and Hanks, 1995) are well-conserved between the Ksr kinases of different species, but differ from those of all other kinases. One peculiarity is found in sub-domain II of the two mammalian proteins. This sub-domain has an invariant lysine residue involved in the phospho-transfer reaction that is conserved in all kinases identified thus far (Hardie and Hanks, 1995), however, both mammalian sequences have an arginine at this position (Table 1). It has been shown that mutagenesis of this lysine residue to any other residue, including arginine, abolishes catalytic function in several kinases (Hanks et al., 1988). However, the sequence conservation between the mouse and the human kinase domains indicates that these enzymes are functional.

Sub-domains VIb and VIII also contain conserved residues that often correlate with hydroxy amino acid recognition (Hanks et al., 1988). For instance, HRDLKXXN (VIb) and T/SXXY/F (VIII) motifs are indicative of Ser/Thr-kinases while HRDLRIAXA/RN'(VIb) and PXXW (VIII) motifs are associated with Tyr-kinases. Based solely on these conserved residues it is not clear to which class Ksr kinases belong (Table 1). Indeed, for sub-domain VIb, the Drosophila sequences have an arginine residue at the critical position (like a Tyr-kinase), while the two mammalian sequences have a lysine residue (like a Ser/Thr-kinase). The sub-domain VIII motif for all the Ksr members is WXXY, which differs from that found in all other kinases.

In the N-terminal region, four Conserved Areas (CA1 to CA4) can be recognized (Table 1). CA1 is a stretch of 40 amino acids located at the very N-terminus of Ksr kinases and has no equivalent in the database. Its conservation and the identification of a mutation in it (ksr$^{S-548}$) indicate that it plays a role in Ksr function. CA2 is a proline-rich stretch followed by basic residues which may correspond to a class II SH3-domain binding site (PXXPXR/K; Alexandropoulos et al., 1995), although the two fly sequences diverge from the consensus by one amino acid. CA3 is a cysteine-rich domain similar to the one found in other signaling molecules, such as the CR1 domain of Raf. Finally, CA4 is rich in serines and threonines and also contains a MAPK consensus phosphorylation site.

A search of current databases indicated that the Raf kinase members are the closest relatives to the Ksr kinases based on sequence similarity within the kinase domain (e.g. 42% identity/61% similarity between the Dm Ksr and Raf kinase domains) and shared structural features in the N-terminal region (Table 1). Both the Raf and Ksr kinases have a related C-terminal 300 amino acid kinase domain, named CA5 and CR3, respectively (CR3; Heidecker et al., 1992). The spacing and sizes of the domains of the Ksr kinases are well conserved, except for the presence of an additional ~100 amino acids between the CA4 and CA5 domains of the Drosophila sequences. In addition, they both have a long N-terminal region that contains a cysteine-rich stretch followed by a serine/threonine-rich region, named CA3 and CA4 for Ksr kinases and CR1 and CR2 for Raf kinases. Ksr and Raf kinases also have distinctive features. For instance, the CA1 and CA2 regions found in Ksr kinases are absent from Raf kinases. The Ras-binding domain (RBD) found in the CR1 domain of Raf kinases (Nassar et al., 1995) is absent from Ksr kinases, which suggests that they are regulated differently. Moreover, interaction assays using the yeast two-hybrid system or bacterially-expressed fusion proteins, did not detect any interaction between Ras1 and Ksr, while similar experiments detected an interaction between Ras1 and the CR1 domain of D-Raf. Finally, amino acids in kinase sub-domain VIII, which are important for substrate recognition, are not conserved between Ksr and Raf kinases suggesting that these kinases have different targets. This is supported by the observation that Ksr failed to interact with Dsor1 (D-MEK) in a yeast two-hybrid assay, whereas, D-Raf and Dsor1 interacted strongly.

Ksr functions in multiple RTK pathways.

Recent evidence suggests that RTKs use a similar set of proteins to transduce their signals to the nucleus (see Background). Several lines of genetic evidence suggest that the Ksr kinase corresponds to a new component of this widely used signal transduction pathway. For instance, adult flies homozygous for the sub-viable allele ksr$^{S-548}$ have rough eyes in which ommatidia are missing both outer (R1–R6) and R7 photoreceptor cells. This suggests that, like Ras1 (Simon et al., 1991), ksr has a broader role than just specification of the R7 cell fate. Using the FLP/FRT system (Xu and Rubin, 1993), we did not recover homozygous mutant tissue for the strong allele ksr$^{S-638}$, which indicates that Ksr is required for cell proliferation or survival. In addition, except for the ksr$^{S-548}$ allele, all ksr alleles are recessive lethal and in most cases they die as third instar larvae and lack imaginal discs. This phenotype is often seen with mutations in genes required for cell proliferation (Gatti and Baker, 1989). RNA in situ hybridization showed that ksr mRNA is ubiquitously distributed and is present throughout embryogenesis, consistent with a general role for this kinase.

We directly tested whether ksr is an essential component of the Torso RTK pathway, another Drosophila RTK-dependent signal transduction cascade (reviewed in Duffy and Perrimon, 1994). Torso initiates a signal transduction cascade required for development of the anterior and posterior extremities of the embryo. As for the Sevenless RTK pathway, genetic screens aimed at elucidating this pathway have led to the identification of drk, sos, Ras1 and genes encoding the downstream cassette of kinases (Raf/MEK/MAPK) as being critical for signal propagation (reviewed in Duffy and Perrimon, 1994). This signal transduction cascade appears to control the expression pattern of two genes, tailless (tll) and huckebein (hkb) at the embryonic termini (reviewed in Duffy and Perrimon, 1994). During the cellular blastoderm stage, the posterior domain of expression of both factors depends uniquely on Torso-mediated signaling thereby providing excellent markers of Torso activity.

Embryos derived from mothers homozygous for a torso null mutation have defective termini. The posterior end is missing all structures beyond the seventh abdominal segment, while the anterior end exhibits severe head skeleton defects (reviewed in Duffy and Perrimon, 1994). Consistent with these abnormalities, aberrant expression patterns are observed for tll and hkb; that is, no tll or hkb expression is detected at the posterior end, while tll expression pattern is extended and hkb is retracted at the anterior end. Embryos derived from germlines homozygous for loss-of-function mutations in general RTK components like drk, sos, Ras1 or D-Raf show similar terminal defects, albeit to various degrees, consistent with their role in Torso RTK-mediated signaling (Hou et al., 1995).

To determine whether ksr acts in the Torso pathway, we used the FLP-FDS system (Hou et al., 1995) to generate ksr germline clones and examined the terminal structures of embryos derived from homozygous mutant oocytes. Like embryos derived from Torso mutant mothers, cuticle preparations of ksr$^{S-638}$ embryos revealed severe terminal defects. They are missing posterior structures beyond the seventh abdominal segment and have collapsed head skeletons. In addition, no tll or hkb expression is detected at the posterior end while a broader domain of tll expression and a reduced one for hkb is observed at the anterior extremity. These results indicate that ksr also functions in the Torso pathway, consistent with Ksr being a general component acting downstream of RTKs.

Activated D-Raf rescues terminal defects observed in embryos derived from germlines homozygous for ksr$^{S-638}$.

The inability of ksr mutants to suppress the sE-Raf$^{Tor4021}$ phenotype in the eye suggested that Ksr functions upstream or in parallel to D-Raf, but not downstream. To clarify where ksr functions relative to D-Raf in the Torso pathway, RNA encoding an activated form of D-Raf (Raf$^{Tor4021}$) was injected into embryos derived from germlines homozygous for ksr$^{S-638}$. If Ksr functions solely upstream of D-Raf then activated D-Raf should rescue the mutant phenotype. In contrast, if Ksr functions solely downstream of D-Raf then injection of activated D-Raf RNA should have no influence on the ksr$^{S-638}$-associated embryonic phenotype. It is also possible that rescue might be observed if Ksr functions in a pathway parallel to D-Raf and can be bypassed by activation of D-Raf to sufficiently high levels. Injection of activated D-Raf partially rescued the ksr$^{S-638}$-associated embryonic terminal defects. These results confirm that Ksr does not act downstream of D-Raf.

Experimental Procedures

Fly culture and crosses were performed according to standard procedures. Clonal analysis in the eye was performed on the ksr$^{S-638}$ allele (the strongest suppressor of sev-Ras1$^{V12}$ among the ksr alleles) using the FLP/FRT system (Xu and Rubin, 1993).

ksr$^{S-638}$ germline clones were generated as described in Hou et al. (1995). Cuticle preparation of embryos was performed as described in Belvin et al. (1995). In situ hybridization was performed according to Dougan and DiNardo (1992) using digoxigenin-labelled RNA probes. Injection of embryos was performed as described in Anderson and Nüsslein-Volhard (1984). An in vitro trancription kit (Promega) was used to synthesize activated D-Raf RNA from the Raf$^{TOR4021}$ DNA template (Dickson et al., 1992).

Scanning electron microscopy was performed as described by Kimmel et al. (1990). Fixation and sectioning of adult eyes were performed as described by Tomlinson and Ready (1987).

The βGGT-I locus was recovered from a chromosome walk initiated by screening a cosmid library (Tamkun et al., 1992) with a genomic fragment flanking a P-element [1(2) 05714] inserted at 25B4-6 (Karpen and Spradling, 1992; Berkeley Drosophila Genome Project, pers. comm.). A 1.7 kb Spe1-Sph1 genomic fragment spanning the S-2126 allele inversion breakpoint was used to screen a Drosophila eye-antennal imaginal disc cDNA library in λgt10. Sixteen related cDNA clones were isolated from ~700,000 pfu screened.

The ksr gene was isolated from a chromosome walk. Genomic blot analysis of X-ray-induced ksr alleles was performed according to standard procedures (Sambrook et al., 1989). The 2.9 kb and 2.2 kb BamHI fragments from cosmid III identified polymorphisms in the S-69 and S-511 alleles, respectively. A 7 kb EcoRI genomic fragment encompassing all of the 2.9 kb BamHI fragment and part of the 2.2kb BamHI fragment was used along with the 2.2kb BamHI fragment to screen ~700,000 phage from a Drosophila eye-antennal imaginal disc cDNA library in λgt10. Seven related cDNA clones were isolated and characterized by sequencing.

A *D. virilis* genomic library was screened at reduced stringency using the Dm Ksr kinase domain as a probe. In brief, filters were hybridized in 5X SSCP; 10X Denhart; 0.1% SDS; 200 µg/ml sonicated salmon sperm DNA at 42° C. for 12 hrs, rinsed several times at room temperature and washed twice for 2 hrs at 50° C. in 1X SSC; 0.1% SDS. 12 genomic clones were identified; one was purified and analyzed by sequencing.

A DNA fragment corresponding to the hb DNA sequence was prepared by PCR from a mouse brain cDNA library and used as a probe to screen a mouse PCC4 teratocarcinoma cDNA library (Stratagene). One full-length cDNA clone, named mKsr-1, was obtained from 1×10$^6$ pfu screened. Using the mKsr-1 kinase domain as a probe, 1×10$^6$ pfu of a human fetal brain cDNA library (Clontech) was hybridized at reduced stringency (see above). Thirteen related cDNA clones were isolated and characterized by sequencing. They all represent partial transcripts and only one of them, named hKsr-1, has a complete kinase domain.

DNA sequences were performed by the dideoxy in termination procedure (Sanger et al., 1977) using the Automated Laser Fluorescence (ALF) system (Pharmacia). Templates were prepared by sonicating plasmid DNA and inserting the sonicated DNA into the M13mp10 vector. The entire coding regions of βGGT-I and Ksr cDNAs from each species were sequenced on both strands as well as the genomic regions that correspond to the βGGT-1 and Dm ksr loci. Sequences were analysed using the Staden (R. Staden, MRC of Molecular Biology, Cambridge UK) and the Genetics Computer Group, Inc. software packages. The chromosomal regions for different βGGT-I and ksr mutant alleles were cloned into the λ_ZAP-express vector (Stratagene) and their respective coding regions were completely sequenced using oligonucleotide primers.

Cited References

Alexandropoulos, K., et al. (1995).Proc. Natl. Acad. Sci. USA 92, 3110–3114.
Altschul, S. F., et al. (1990) J. Mol. Biol. 215, 403–410.
Anderson, K. V. and Nüsslein-Volhard, C. (1984). Nature 311, 223–227.
Belvin, M. P., Jin, Y. and Anderson, K. V. (1995). Genes Dev. 9, 783–793.
Bier, E., et al. (1989). Genes Dev. 3, 1273–1287.
Bruder, J. T., Heidecker, B. and Rapp, U. R. (1992). Genes Dev. 6, 545–556.
Burgering, B. M. T. and Bos, J. L. (1995). Trends Biochem. Sci. 20, 18–22.
Buss, J. E., et al. (1989).Science 243, 1600–1603.
Cano, E. and Mahadevan, L. C. (1995). Trends Biochem. Sci. 20, 117–122.
Daum, G., et al. (1994).Trends Biochem. Sci. 19, 474–480.
Dent, P., et al. (1995). Science 268, 1902–1906.
Dent, P. and Sturgill, T. W. (1994). Proc. Natl. Acad. Sci. USA 91, 9544–9548.
Dickson, B., et al. (1992), Nature 360, 600–603.
Dougan, S. and DiNardo, S. (1992). Nature 360, 347–350.
Duffy, J. B. and Perrimon, N. (1994). Dev. Biol. 166, 380–395.
Fortini, M. E., Simon, M. A. and Rubin, G. M. (1992). Nature 355, 559–561.
Gatti, M. and Baker, B. S. (1989). Genes Dev. 3, 438–453.
Glomset, J. A. and Farnsworth, C. C. (1994). Annu. Rev. Cell Biol. 10, 181–205.
Hanks, S. K., Quinn, A. M. and Hunter, T. (1988). Science 241, 42–52.
Hardie, G.and Hanks, S. Eds. (1995). The protein kinase (part I): protein-serine kinases. (FactsBook Series, Academic Press inc.).
Heidecker, G., Kolch, W., Morrison, D. K. and Rapp, U. R. (1992). Adv. Can. Res. 58, 53–73.
Hou, X. S., Chou, T. B., Melnick, M. B. and Perrimon, N. (1995). Cell 81, 63–71.
Hubbard, S. R., et al. (1991). Science 254, 1776–1779.
Karpen, G. H. and Spradling, A. C. (1992). Genetics 132, 737–753.
Kato, K., et al. (1992). Proc. Natl. Acad. Sci.USA 89, 6403–6407.
Kimmel, B. E., Heberlein, U. and Rubin, G. M. (1990). Genes Dev. 4, 712–727.
Marshall, C. J. (1993). Science 259, 1865–1866.
Marshall, C. J. (1994). Curr. Opin. Genet. Dev. 4, 82–89.
McCormick, F. (1994a). Curr. Opin. Genet. Dev. 4, 71–76.
McCormick, F. (1994b).Trends Cell Biol. 4, 347–350.
Nassar, N., et al. (1995). Nature 375, 554–560.
Nehls, M., et al. (1994) (Genbank accession number X81634)
Sambrook, J., Fritsch, E. F. and Maniatis, T. (1989). Molecular Cloning: A Laboratory Manual Second Edition (Cold Spring Harbor, New York: Cold Spring Harbor Laboratory Press).
Sanger, F., Nicklen, S. and Coulson, A. (1977). Proc. Natl. Acad. Sci. USA 74, 5463–5467.
Sidow, A. and Thomas, W. K. (1994) Curr. Biol. 4, 596–603.
Simon, M. A., et al. (1991). Cell 67,701–716.

Simon, M. A., et al. (1985). Cell 42, 831–840.
Tamkun, J. W., et al. (1992). Cell 68, 561–572.
Tomlinson, A. and Ready, D. F. (1987). Dev. Biol. 123, 264–275.
van der Geer, P., et al. (1994). Annu. Rev. Cell Biol. 10, 251–337.
White, M. A., et al. (1995). Cell 80, 533–541.
Willumsen, B. M., et al. (1984). EMBO J. 3, 2581–2585.
Xu, T. and Rubin, G. M. (1993). Development 117, 1223–1237.

Pharmaceutical lead compound screening assays.

1. Protocol for Ksr—substrate phosphorylation assay.
    A. Reagents:
      Neutralite Avidin: 20 µg/ml in PBS.
      hKsr: $10^{-8}$–$10^{-5}$ M hKsr at 20 µg/ml in PBS.
      Blocking buffer: 5% BSA, 0.5% Tween 20 in PBS; 1 hour at room temperature.
      Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
      [$^{32}$P]γ-ATP 10x stock: $2\times10^{-5}$ M cold ATP with 100 µCi [$^{32}$P]γ-ATP. Place in the 4° C. microfridge during screening.
      Substrate: $2\times10^{-6}$ M biotinylated synthetic peptide kinase substrate (MBP, Sigma) at 20 µg/ml in PBS.
      Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
    B. Preparation of assay plates:
      Coat with 120 µl of stock Neutralite avidin per well overnight at 4° C.
      Wash 2 times with 200 µl PBS.
      Block with 150 µl of blocking buffer.
      Wash 2 times with 200 µl PBS.
    C. Assay:
      Add 40 µl assay buffer/well.
      Add 40 µl hKsr (0.1–10 pmoles/40 ul in assay buffer)
      Add 10 µl compound or extract.
      Shake at 30° C. for 15 minutes.
      Add 10 µl [$^{32}$P]γ-ATP 10x stock.
      Add 10 µl substrate.
      Shake at 30° C. for 15 minutes.
      Incubate additional 45 minutes at 30° C.
      Stop the reaction by washing 4 times with 200 µl PBS.
      Add 150 µl scintillation cocktail.
      Count in Topcount.
    D. Controls for all assays (located on each plate):
      a. Non-specific binding (no hKsr added)
      b. cold ATP to achieve 80% inhibition.

2. Protocol for hKsr-Raf binding assay.
    A. Reagents:
      Anti-myc antibody: 20 µg/ml in PBS.
      Blocking buffer: 5% BSA, 0.5% Tween 20 in PBS; 1 hour at room temperature.
      Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.
      $^{33}$P hKsr 10x stock: $10^{8}$–$10^{6}$ M "cold" hKsr (full length) supplemented with 200,000–250,000 cpm of labeled hKsr (HMK-tagged) (Beckman counter). Place in the 4° C. microfridge during screening.
      Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (3MB #1017128), 10 mg APMSF (BMB #917575), and 2 mM NaVo$_3$ (Sigma #S-6508) in 10 ml of PBS.
      Raf: b $10^{-8}$–$10^{-5}$ M myc eptitope-tagged Raf in PBS.
    B. Preparation of assay plates:
      Coat with 120 µl of stock anti-myc antibody per well overnight at 4° C.
      Wash 2X with 200 µl PBS.
      Block with 150 µl of blocking buffer.
      Wash 2X with 200 µl PBS.
    C. Assay:
      Add 40 µl assay buffer/well.
      Add 10 µl compound or extract.
      Add 10 µl $^{33}$P-hKsr (20,000–25,000 cpm/0.1–10 pmoles/well =$10^{-9}$–$10^{-7}$ M final concentration).
      Shake at 25° C. for 15 minutes.
      Incubate additional 45 minutes at 25 ° C.
      Add 40 µl eptitope-tagged Raf (0.1–10 pmoles/40 ul in assay buffer)
      Incubate 1 hour at room temperature.
      Stop the reaction by washing 4 times with 200 µl PBS.
      Add 150 µl scintillation cocktail.
      Count in Topcount.
    D. Controls for all assays (located on each plate):
      a. Non-specific binding (no hKsr added)
      b. Soluble (non-tagged Raf) to achieve 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying compounds which modulate the binding of a kinase suppressor of ras (Ksr) to a natural intracellular binding target, said method comprising the steps of:

forming a mixture comprising:
a Ksr,
a natural intracellular Ksr binding target, and
a candidate agent;
incubating said mixture under conditions whereby, but for the presence of said agent, said Ksr selectively binds said binding target at a first binding affinity;
detecting a second binding affinity of said Ksr to said binding target,
wherein a difference between said first and second binding affinity indicates that said agent modulates the binding of a Ksr to a natural intracellular binding target.

2. A method according to claim 1, wherein said Ksr binding target comprises a 14-3-3 gene product.

3. A method according to claim 1, wherein said Ksr binding target comprises a Ksr protein.

4. A method of identifying agents which modulate the phosphorylation of a substrate by a kinase suppressor of ras (Ksr), said method comprising the steps of:

forming a mixture comprising:
a Ksr,
a Ksr substrate, and
a candidate agent;
incubating said mixture under conditions whereby, but for the presence of said agent, said Ksr selectively phosphorylates said substrate at a first rate;
detecting a second rate of phosphorylation of said substrate by said Ksr,
wherein a difference between said first and second rate indicates that said agent modulates the phosphorylation of a Ksr substrate by a Ksr.

5. A method according to claim 1 wherein said Ksr substrate comprises a 14-3-3 gene product.

6. A method according to claim 4 wherein said Ksr substrate comprises a Ksr protein.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

(i) SEQUENCE CHARACTERISTICS:
  (A) LENGTH: 3697 base pairs
  (B) TYPE: nucleic acid
  (C) STRANDEDNESS: double
  (D) TOPOLOGY: linear (ii) MOLECULE TYPE: cDNA (xi) SEQUENCE DESCRIPTION: SEQ ID NO:1:

| | | | | | | |
|---|---|---|---|---|---|---|
| GAATTCCAAT | TATTGCTTTT | TCGCATTGCC | TAAGCCGTTT | AGAGTTGCGG | GCGTTAGCGT | 60 |
| GCGCGATAGC | CGGAGCACCG | AACGTCAAGG | TCGCTTGGCG | AGGGCCACAA | TGCGGGGCGG | 120 |
| AGTCCCAGCC | ATTGGTCCCA | TCGAATCGTC | GAGTCCCCGA | GAGGGCGTCT | GAAAAAATCA | 180 |
| ATCGGGCTCC | ACTCCGTCGC | GAATAAGCAG | GATGAGCAGC | AACAACAACG | CACCCGCATC | 240 |
| GGCTCCAGAC | ACGGGCTCCA | CCAATGCCAA | CGATCCCATC | TCCGGTTCGC | TGTCCGTAGA | 300 |
| CAGCAACCTG | GTTATCATTC | AGGACATGAT | TGATCTCTCG | GCCAACCATC | TGGAGGGCCT | 360 |
| GCGAACGCAG | TGCGCGATCA | GCTCCACGCT | GACGCAGCAG | GAGATTCGTT | GCCTGGAGTC | 420 |
| GAAGCTGGTG | CGATACTTCT | CCGAGCTGCT | GCTGGCGAAG | ATGCGGCTAA | ATGAGCGCAT | 480 |
| CCCGGCCAAC | GGGCTTGTGC | CCACACAAC | GGGCAACGAA | CTGAGGCAAT | GGCTGCGCGT | 540 |
| AGTGGGCCTT | AGCCAGGGGA | CTCTTACCGC | CTGCCTTGCT | CGCCTGACCA | CTCTAGAGCA | 600 |
| AAGCCTGCGT | CTCAGCGACG | AGGAGATCCG | TCAACTCCTG | GCTGACAGCC | CAGCCAGCG | 660 |
| AGAGGAGGAG | GAACTGCGAC | GCCTGACCAG | GGCCATGCAG | AACTTAAGGA | AGTGCATGGA | 720 |
| GTCGCTGGAG | AGCGGTACTG | CGGCTAGCAA | CAACGATCCA | GAGCAGTGGC | ACTGGGACTC | 780 |
| CTGGACAGG | CCCACCCACA | TTCATCGCGG | CAGTGTGGGA | AACATTGGAC | TGGGTAACAA | 840 |
| TTCAACCGCC | TCCCCGAGAA | CCCATCATCG | CCAGCATGGT | GTCAAGGGAA | AGAATTCCGC | 900 |
| TCTGGCCAAC | TCCACCAACT | TCAAAAGTGG | CCGCCAATCG | CCCTCAGCGA | CAGAAGAGCT | 960 |
| GAACAGCACA | CAGGGTTCCC | AGCTGACTTT | AACCCTTACG | CCCTCGCCAC | CCAATTCGCC | 1020 |
| CTTCACGCCT | TCCAGTGGGC | TGAGCAGCAG | CCTTAATGGA | ACACCACAGA | GGAGTCGTGG | 1080 |
| TACCCCGCCG | CCAGCCAGAA | AGCACCAGAC | CTTGCTGAGC | CAGAGTCATG | TGCAAGTGGA | 1140 |
| CGGGGAGCAA | TTAGCCCGCA | ACCGTTTGCC | CACTGATCCC | AGCCCCGATA | GCCACAGCTC | 1200 |
| CACCAGCTCG | GACATCTTTG | TGGACCCAAA | TACTAATGCC | AGCTCCGGAG | GAAGTTCCTC | 1260 |
| GAACGTGCTT | ATGGTGCCAT | GCTCTCCGGG | CGTGGGTCAC | GTGGGCATGG | GTCATGCAAT | 1320 |
| CAAGCATCGT | TTCACCAAGG | CCCTGGGCTT | CATGGCCACC | TGTACCCTGT | GCCAGAAGCA | 1380 |
| GGTCTTTCAC | CGCTGGATGA | AGTGCACCGA | CTGCAAGTAC | ATCTGCCACA | AGTCATGCGC | 1440 |
| ACCGCACGTA | CCGCCCTCCT | GTGGACTTCC | ACGAGAATAT | GTGGACGAGT | TCGGCACAT | 1500 |
| AAAGGAGCAG | GGAGGATACG | CCAGTCTGCC | GCATGTGCAT | GGCGCGGCGA | AAGGATCCCC | 1560 |
| TTTGGTAAAA | AAGAGCACCC | TGGGTAAGCC | CTTGCATCAG | CAGCACGGCG | ATAGCAGTTC | 1620 |
| GCCGAGTTCC | AGCTGCACTA | GTTCCACGCC | CAGCAGTCCG | GCGCTGTTCC | AGCAAAGGGA | 1680 |
| GCGCGAGCTG | GATCAGGCGG | GCAGCAGCTC | TAGCGCCAAT | CTGTTACCTA | CGCCTTCGCT | 1740 |
| TGGCAAGCAC | CAGCCGAGTC | AATTCAACTT | TCCCAACGTG | ACGGTGACGA | GCAGTGGCGG | 1800 |
| AAGCGGTGGT | GTATCGCTCA | TCTCCAATGA | ACCAGTGCCA | GAGCAATTCC | CCACGGCGCC | 1860 |
| TGCAACAGCC | AACGGAGGAC | TTGATAGTCT | GGTGAGCAGC | TCCAACGGGC | ACATGAGCTC | 1920 |
| GCTCATCGGT | AGCCAAACTT | CAAACGCTTC | TACTGCGGCC | ACCTTGACGG | GCAGTCTGGT | 1980 |
| CAATAGCACA | ACCACCACCA | GCACCTGCAG | TTTCTTTCCG | CGAAAATTGA | GCACAGCCGG | 2040 |
| TGTGGATAAG | AGGACGCCGT | TCACCAGCGA | GTGCACGGAT | ACCCACAAGT | CAAATGACAG | 2100 |

-continued

| | | | | | |
|---|---|---|---|---|---|
| CGACAAGACA | GTCTCCTTGT | CTGGAAGTGC | CAGCACGGAC | TCGGACCGGA | CACCCGTTCG | 2160 |
| TGTGGATTCA | ACGGAAGACG | GAGACTCGGG | ACAATGGCGA | CAGAACTCGA | TCTCACTCAA | 2220 |
| GGAATGGGAC | ATCCCGTATG | GTGATCTGCT | TCTGCTCGAG | CGGATAGGGC | AGGGACGCTT | 2280 |
| CGGCACCGTG | CATCGAGCCC | TTTGGCACGG | AGATGTGGCG | GTTAAGCTGC | TCAACGAGGA | 2340 |
| CTATCTGCAA | GACGAACACA | TGCTGGAGAC | GTTTCGCAGC | GAGGTAGCCA | ACTTCAAGAA | 2400 |
| CACTCGACAC | GAGAACCTGG | TGCTGTTCAT | GGGAGCCTGC | ATGAACCCAC | ATATTTGGC | 2460 |
| CATTGTGACT | TCATTGTGCA | AGGGCAACAC | CTTGTATACG | TATATTCACC | AGCGTCGGGA | 2520 |
| GAAGTTTGCC | ATGAACCGGA | CTCTCCTCAT | TGCCCAGCAG | ATCGCCCAGG | GCATGGGCTA | 2580 |
| CCTGCACGCA | AGGGAGATCA | TCCACAAAGA | TCTGCGCACC | AAGAACATCT | TCATCGAGAA | 2640 |
| CGGCAAGGTG | ATTATCACGG | ACTTTGGGCT | GTTCAGCTCC | ACCAAGCTGC | TCTACTGTGA | 2700 |
| TATGGGCCTA | GGAGTGCCCC | ACAACTGGTT | GTGCTACCTG | GCGCCGGAGC | TAATCCGAGC | 2760 |
| ATTGCAGCCG | GAGAAGCCGC | GTGGAGAGTG | TCTGGAGTTC | ACCCCATACT | CCGATGTCTA | 2820 |
| CTCTTTCGGA | ACCGTTTGGT | ACGAGCTAAT | CTGCGGCGAG | TTCACATTCA | AGGATCAGCC | 2880 |
| GGCGGAATCG | ATCATCTGGC | AGGTTGGCCG | TGGGATGAAG | CAGTCGCTGG | CCAACCTGCA | 2940 |
| GTCTGGACGG | GATGTCAAGG | ACTTGCTGAT | GCTGTGCTGG | ACCTACGAGA | GGAGCACCG | 3000 |
| GCCGCAGTTC | GCACGCCTGC | TCTCCCTGCT | GGAGCATCTT | CCCAAGAAGC | GTCTGGCGCG | 3060 |
| CAGTCCCTCC | CACCCCGTCA | ACCTTTCCCG | TTCGCCGAG | TCCGTGTTCT | GAGGGAACTG | 3120 |
| CAGCATGGCC | ACTGTCACTG | TCTAGTACAA | TTTCGATCTA | CCAACTAAGC | TAGCTCGCTT | 3180 |
| TGTGCCCTCG | TCCACTCTAC | ACAAACTCTC | TCCCAAGGCG | AAGTTCTATC | GAGCCGAGCG | 3240 |
| AAGATTGTAA | ATACATAAAC | GTAACTACCA | AATTATAGCA | ATCCATTTTA | AAAACTACAT | 3300 |
| ACATATGTGT | AGGCATGTAT | CGGGAGCACT | CCAGTTGCAG | TTGTTAGCAA | ACGAAACAAA | 3360 |
| GGCAAATCAA | ATGTTAACTC | GAAAAAGACA | AAACGCTTAA | ATGTTTAAGA | GCAGAGGCAA | 3420 |
| ACAGAGAAGG | CATAGACATA | CATATACAAA | CAAACAAACA | AGCACTGTGG | CAAACATAAA | 3480 |
| TGTAAACGTT | AATCAGGTGA | GCAATTTCTA | AATTGTTAAT | TATGTGTAAG | AGAACTATAT | 3540 |
| ATATATATAT | ATATATATAT | ATATATATAT | ATATACATGT | ATATACAGCA | GCAATGTATT | 3600 |
| GTATGACG | GACTAGTGTT | AAATTAAATA | TATATTGTGA | ATTATGTATG | GTCAAGTGTA | 3660 |
| TATAGTAAAT | GGACTTTAAA | TGCGAAATCG | GGAATTC | | | 3697 |

( 2 ) INFORMATION FOR SEQ ID NO:2:

( i ) SEQUENCE CHARACTERISTICS:
        ( A ) LENGTH: 966 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

```
Met Ser Ser Asn Asn Asn Ala Pro Ala Ser Ala Pro Asp Thr Gly Ser
 1               5                  10                  15

Thr Asn Ala Asn Asp Pro Ile Ser Gly Ser Leu Ser Val Asp Ser Asn
            20                  25                  30

Leu Val Ile Ile Gln Asp Met Ile Asp Leu Ser Ala Asn His Leu Glu
        35                  40                  45

Gly Leu Arg Thr Gln Cys Ala Ile Ser Ser Thr Leu Thr Gln Gln Glu
    50                  55                  60

Ile Arg Cys Leu Glu Ser Lys Leu Val Arg Tyr Phe Ser Glu Leu Leu
```

```
            65                    70                      75                      80
    Leu Ala Lys Met Arg Leu Asn Glu Arg Ile Pro Ala Asn Gly Leu Val
                    85                  90                  95
    Pro His Thr Thr Gly Asn Glu Leu Arg Gln Trp Leu Arg Val Val Gly
                    100             105                 110
    Leu Ser Gln Gly Thr Leu Thr Ala Cys Leu Ala Arg Leu Thr Thr Leu
                115                 120                 125
    Glu Gln Ser Leu Arg Leu Ser Asp Glu Ile Arg Gln Leu Leu Ala
            130                 135                 140
    Asp Ser Pro Ser Gln Arg Glu Glu Glu Leu Arg Arg Leu Thr Arg
    145                 150                 155                 160
    Ala Met Gln Asn Leu Arg Lys Cys Met Glu Ser Leu Glu Ser Gly Thr
                        165                 170                 175
    Ala Ala Ser Asn Asn Asp Pro Glu Gln Trp His Trp Asp Ser Trp Asp
                        180             185                 190
    Arg Pro Thr His Ile His Arg Gly Ser Val Gly Asn Ile Gly Leu Gly
                195                 200                 205
    Asn Asn Ser Thr Ala Ser Pro Arg Thr His His Arg Gln His Gly Val
    210                 215                 220
    Lys Gly Lys Asn Ser Ala Leu Ala Asn Ser Thr Asn Phe Lys Ser Gly
    225                 230                 235                 240
    Arg Gln Ser Pro Ser Ala Thr Glu Glu Leu Asn Ser Thr Gln Gly Ser
                    245                 250                 255
    Gln Leu Thr Leu Thr Leu Thr Pro Ser Pro Pro Asn Ser Pro Phe Thr
                    260                 265                 270
    Pro Ser Ser Gly Leu Ser Ser Ser Leu Asn Gly Thr Pro Gln Arg Ser
                275                 280                 285
    Arg Gly Thr Pro Pro Pro Ala Arg Lys His Gln Thr Leu Leu Ser Gln
    290                 295                 300
    Ser His Val Gln Val Asp Gly Glu Gln Leu Ala Arg Asn Arg Leu Pro
    305                 310                 315                 320
    Thr Asp Pro Ser Thr Asp Ser His Ser Ser Thr Ser Ser Asp Ile Phe
                    325                 330                 335
    Val Asp Pro Asn Thr Asn Ala Ser Ser Gly Gly Ser Ser Ser Asn Val
                    340                 345                 350
    Leu Met Val Pro Cys Ser Pro Gly Val Gly His Val Gly Met Gly His
                355                 360                 365
    Ala Ile Lys His Arg Phe Thr Lys Ala Leu Gly Phe Met Ala Thr Cys
        370                 375                 380
    Thr Leu Cys Gln Lys Gln Val Phe His Arg Trp Met Lys Cys Thr Asp
    385                 390                 395                 400
    Cys Lys Tyr Ile Cys His Lys Ser Cys Ala Pro His Val Pro Pro Ser
                    405                 410                 415
    Cys Gly Leu Pro Arg Glu Tyr Val Asp Glu Phe Arg His Ile Lys Glu
                420                 425                 430
    Gln Gly Gly Tyr Ala Ser Leu Pro His Val His Gly Ala Ala Lys Gly
                435                 440                 445
    Ser Pro Leu Val Lys Lys Ser Thr Leu Gly Lys Pro Leu His Gln Gln
        450                 455                 460
    His Gly Asp Ser Ser Ser Pro Ser Ser Ser Cys Thr Ser Ser Thr Pro
    465                 470                 475                 480
    Ser Ser Pro Ala Leu Phe Gln Gln Arg Glu Arg Glu Leu Asp Gln Ala
                    485                 490                 495
```

| | | | | | | | | | | | | | | |
|---|---|---|---|---|---|---|---|---|---|---|---|---|---|---|
| Gly | Ser | Ser | Ser 500 | Ser | Ala | Asn | Leu | Leu 505 | Pro | Thr | Pro | Ser 510 | Leu | Gly | Lys |
| His | Gln | Pro 515 | Ser | Gln | Phe | Asn | Phe 520 | Pro | Asn | Val | Thr | Val 525 | Thr | Ser | Ser |
| Gly | Gly 530 | Ser | Gly | Gly | Val | Ser 535 | Leu | Ile | Ser | Asn | Glu 540 | Pro | Val | Pro | Glu |
| Gln 545 | Phe | Pro | Thr | Ala | Pro 550 | Ala | Thr | Ala | Asn | Gly 555 | Gly | Leu | Asp | Ser | Leu 560 |
| Val | Ser | Ser | Ser | Asn 565 | Gly | His | Met | Ser | Ser 570 | Leu | Ile | Gly | Ser | Gln 575 | Thr |
| Ser | Asn | Ala | Ser 580 | Thr | Ala | Ala | Thr | Leu 585 | Thr | Gly | Ser | Leu | Val 590 | Asn | Ser |
| Thr | Thr | Thr 595 | Thr | Ser | Thr | Cys | Ser 600 | Phe | Phe | Pro | Arg | Lys 605 | Leu | Ser | Thr |
| Ala | Gly 610 | Val | Asp | Lys | Arg | Thr 615 | Pro | Phe | Thr | Ser | Glu 620 | Cys | Thr | Asp | Thr |
| His 625 | Lys | Ser | Asn | Asp | Ser 630 | Asp | Lys | Thr | Val | Ser 635 | Leu | Ser | Gly | Ser | Ala 640 |
| Ser | Thr | Asp | Ser | Asp 645 | Arg | Thr | Pro | Val | Arg 650 | Val | Asp | Ser | Thr | Glu 655 | Asp |
| Gly | Asp | Ser | Gly 660 | Gln | Trp | Arg | Gln | Asn 665 | Ser | Ile | Ser | Leu | Lys 670 | Glu | Trp |
| Asp | Ile | Pro 675 | Tyr | Gly | Asp | Leu | Leu 680 | Leu | Leu | Glu | Arg | Ile 685 | Gly | Gln | Gly |
| Arg | Phe 690 | Gly | Thr | Val | His | Arg 695 | Ala | Leu | Trp | His | Gly 700 | Asp | Val | Ala | Val |
| Lys 705 | Leu | Leu | Asn | Glu | Asp 710 | Tyr | Leu | Gln | Asp | Glu 715 | His | Met | Leu | Glu | Thr 720 |
| Phe | Arg | Ser | Glu | Val 725 | Ala | Asn | Phe | Lys | Asn 730 | Thr | Arg | His | Glu 735 | Asn | Leu |
| Val | Leu | Phe | Met 740 | Gly | Ala | Cys | Met | Asn 745 | Pro | Pro | Tyr | Leu | Ala 750 | Ile | Val |
| Thr | Ser | Leu 755 | Cys | Lys | Gly | Asn | Thr 760 | Leu | Tyr | Thr | Tyr | Ile 765 | His | Gln | Arg |
| Arg | Glu 770 | Lys | Phe | Ala | Met | Asn 775 | Arg | Thr | Leu | Leu | Ile 780 | Ala | Gln | Gln | Ile |
| Ala 785 | Gln | Gly | Met | Gly | Tyr 790 | Leu | His | Ala | Arg | Glu 795 | Ile | Ile | His | Lys | Asp 800 |
| Leu | Arg | Thr | Lys | Asn 805 | Ile | Phe | Ile | Glu | Asn 810 | Gly | Lys | Val | Ile | Ile 815 | Thr |
| Asp | Phe | Gly | Leu 820 | Phe | Ser | Ser | Thr | Lys 825 | Leu | Leu | Tyr | Cys | Asp 830 | Met | Gly |
| Leu | Gly | Val 835 | Pro | His | Asn | Trp | Leu 840 | Cys | Tyr | Leu | Ala | Pro 845 | Glu | Leu | Ile |
| Arg | Ala 850 | Leu | Gln | Pro | Glu | Lys 855 | Pro | Arg | Gly | Glu | Cys 860 | Leu | Glu | Phe | Thr |
| Pro 865 | Tyr | Ser | Asp | Val | Tyr 870 | Ser | Phe | Gly | Thr | Val 875 | Trp | Tyr | Glu | Leu | Ile 880 |
| Cys | Gly | Glu | Phe | Thr 885 | Phe | Lys | Asp | Gln | Pro 890 | Ala | Glu | Ser | Ile | Ile 895 | Trp |
| Gln | Val | Gly | Arg 900 | Gly | Met | Lys | Gln | Ser 905 | Leu | Ala | Asn | Leu | Gln 910 | Ser | Gly |
| Arg | Asp | Val 915 | Lys | Asp | Leu | Leu | Met 920 | Leu | Cys | Trp | Thr | Tyr 925 | Glu | Lys | Glu |

| His | Arg | Pro | Gln | Phe | Ala | Arg | Leu | Leu | Ser | Leu | Leu | Glu | His | Leu | Pro |
|---|---|---|---|---|---|---|---|---|---|---|---|---|---|---|---|
| | 930 | | | | | 935 | | | | | 940 | | | | |

| Lys | Lys | Arg | Leu | Ala | Arg | Ser | Pro | Ser | His | Pro | Val | Asn | Leu | Ser | Arg |
|---|---|---|---|---|---|---|---|---|---|---|---|---|---|---|---|
| 945 | | | | | 950 | | | | | 955 | | | | | 960 |

| Ser | Ala | Glu | Ser | Val | Phe |
|---|---|---|---|---|---|
| | | | | 965 | |

( 2 ) INFORMATION FOR SEQ ID NO:3:

( i ) SEQUENCE CHARACTERISTICS:
        ( A ) LENGTH: 3681 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
CCCCCAAAAA CTATAAAATT TTTCGCGTTT TTCTCATAGC AGAAGCTGTC TCGAAGTCCG      60
CATTTCGCAG GACTGTTCAT GTGTGCTTGC AGCAAGCGAA AAAAGCTGGT TGATGTGGAC     120
AGAATGTGTG TCAAAGTGGT GCAAACAACA AATGATTTGT AAGTGCGTCT GAAAAAATCA     180
ATCAGTTTGT ACTGCTGGAA GGGGCGGGCG GCCACAACA AAATGAGCAG CAGCGCCGCC      240
GCCCAGCTGA CTGCGCCGCC AGTCAGCAAC AGCAACAGCA GCAGCAGTAA CAACAATACA     300
ACAACGACTG CGAGCGAAAG CAATCTAATC ATCATACAGG ATATGATTGA TCTCTCGGCC     360
AACCATCTGG AGGGTCTGCG AACACAGTGC GCAACGAGCG CGACGTTGAC GCAACAGGAG     420
ATCCGCTGCC TAGAGTCCAA GTTGGTGCGC TACTTCTCCG AACTGCTCTT GACCAAAACG     480
AGACTCAACG AACGCATACC CGCGAACGGT CTGCTGCCCC ATCATCAGGC TACCGGGAAC     540
GAGTTGCGCC AATGGCTGCG AGTAGTTGGA CTCAGTCCGG AGTCACTGAA TGCATGCCTA     600
GCGCGTCTAA CGACATTGGA GCAAACACTG CAGCTGAGCG ATGAAGAACT GAAACAACTG     660
CTTGCCCACA ATTCAAGTAC CCAGCTGGAC GAGGAACTGC GGCGGCTGAC CAAAGCGATG     720
CATAATCTCC GAAAATGCAT GGAAACGCTG GACAGCAGCG GCGCAGTTGC GTCCAACGTC     780
GATCCGGAAC AATGGCACTG GGACTCCTGG GATCGACCCC ATCCGCATCA CATGCACCGC     840
GGCAGCATTG GCAATATTGG CCTAGGACTA AGCAGCGCCT CACCTCGCGC CCATCATCGT     900
CAACATCAAC ATCAACACGC GAACAGCAAG CCGAAAATTG TTAACAATTC TGCCTCAAGC     960
TCCCGCAGCG AACAGCAACC ACTGACTGGT TCTCAGTTGA CCTTAACACT GACGCCCTCG    1020
CCACCCAACT CGCCCTTTAC GCCCGCCTCA GGGACGGCAT CCGCCAGCGG CACTCCGCAG    1080
CGCAGCCGCA GTACCACAAC AGCGGCGGGA ACGCCACCAC CAGCCAAGAA GCATCAAACG    1140
CTGCTCATGC ACAACAGCAG CGCTTCGGAA ACGGCACTCG CGGAGCAGCC TCCACGGCCA    1200
CCGCGCAGCC GTCTACCCAC AGATCCTAGC CCGGATAGCC ACAGCTCGGC CAGCAGTTCG    1260
GACATTTTTG TGGACGGTGG CAGTATCAAC AGCTCCAATG TACTACTAGT GCCGCCCTCG    1320
CCAGGTGTGG CACACGTGGG CATGGGTCAT ACCATTAAGC ACCGTTTCAG TAAATGGTTT    1380
GGCTTCATGG CCACGTGCAA ACTGTGCCAA AAGCAGATGA TGAGCCACTG GTTCAAGTGC    1440
ACCGACTGCA AATATATTTG CCACAAGTCC TGTGCGCCGC ATGTGCCGCC CTCGTGTGGC    1500
CTTCCACCCG AATATGTTCA CGAGTTTCGT CAAACTCAGG TGGGCGGCAG ATGGGACCCT    1560
GCGCAGCACA GCAGCAGCAA GGCATCACCA GTGCCCAGGA AGAGCACGCT GGGCAAACCG    1620
CAATTGCAGC AGCCACAGCT GCAGCACGGG GACAGCAGCT CACCAAGCTC GAGCTGCACC    1680
AGCTCAACGC CCAGCAGTCC AGCATTGTTC CAGCAGCAGC AACTGCAACT GGCCACGCCC    1740
```

```
AGCGCCTGCC AGCCGAAACC AGCACCAGCA GCGGTAGCAG CAGCAGCAAC ACAACAGGGT    1800
CAACAGAGTC AATTCAATTT CCCCAACGTG ACCATCACAA GCATCAATGC CTGCAATAGT    1860
AACGCCAGCG CTGCCCAAAC GCTCATATCC AATGAGCCGC AAGCGCATAT GGCCACAACG    1920
GAGTCCACGC TGACCAATGG CAACAACAAC AGCAGCTCCA ACAACGGGAG CAGCGCCAAC    1980
AACAATAGCA GCAGCAGCAG CAGCTGCTCC AATGGTCACC TGCACTCGCT GACTGGAAGT    2040
CAAGTGTCCA CGCATTCGGC TACCTCGCAA GTGTCGAATG TCAGTGGCAG CAGCTCGGCC    2100
ACCTACACCT CCAGTCTGGT GAACAGCGGC AGTTTCTTTC CGCGGAAATT GAGCAATGCT    2160
GGCGTGGACA AGCGGGTGCC CTTTACCAGC GAATATACGG ACACGCACAA GTCGAATGAT    2220
AGCGACAAGA CGGTTTCGTT GTCGGGCAGC GCCAGCACTG ACTCGGATCG CACGCCTGTG    2280
CGTTTGGACT CCACAGAGGA TGGCGACTCG GGCCAATGGC GGCAGAACTC CATATCATTG    2340
AAGGAATGGG ATATACCCTA TGGCGATTTG CACTTGCTGG AGCGCATTGG ACAGGGTCGA    2400
TTTGGCACCG TGCATCGGGC ACTGTGGCAT GGCGATGTCG CTGTGAAGCT GCTCAATGAA    2460
GACTATCTGC AGGACGAGCA CATGCTGGAA TCGTTTCGCA ACGAGGTGGC CAATTTCAAG    2520
AAGACGCGAC ACGAGAATCT GGTGCTGTTC ATGGGCGCCT GCATGAATCC GCCGTATTTG    2580
GCCATTGTCA CGGCACTATG CAAGGGCAAC ACCCTGTACA CCTATATACA TCAGCGAAGG    2640
GAGAAGTTTG CAATGAATCG CACGTTGTTG ATTGCCCAAC AGATTGCCCA GGGCATGGGC    2700
TATTTGCATG CCAGGGACAT AATACACAAG GATCTGCGCA CCAAGAACAT TTTTATAGAG    2760
AATGGCAAGG TGATCATTAC GGACTTTGGC CTATTCAGCT CCACAAAGCT GCTGTACTGT    2820
GATATGGGCT TGGGTGTTCC ACAAAACTGG CTCTGCTACC TGGCCCCGGA ACTAATACGC    2880
GCCCTGCAGC CGTGCAAGCC ACCCGGCGAG TGTCTAGAGT TCACGTCCTA CTCGGATGTT    2940
TACTCATTTG GCACCGTTTG GTACGAGCTA ATTTGCGGCG AATTCACGTT CAAGGATCAA    3000
CCGGCGGAGT CAATCATTTG GCAAGTGGGG CGCGGCATGA ACAGTCGCT  GGCCAATCTG    3060
CAGTCTGGTC GTGATGTCAA GGACCTGCTG ATGCTGTGCT GGACCTATGA AAAGGAGCAC    3120
AGGCCGGACT TTGCACGTCT GCTCTCCTTG CTGGAGCATT TGCCAAAGAA GCGCCTGGCA    3180
CGCAGTCCCT CGCATCCTGT CAACCTCTCG CGCTCAGCGG AATCTGTATT CTAACCAGCC    3240
GATATACAAA TATATACGTT TATAGACAAA TATGTCATAT ATGTAAGCAG GCGCGCACAC    3300
ACTCACACAC ACACACACTC TATTTAGCAC AATTTCACGT TATATGTAAA TGTAAGCTAC    3360
ACACATATGC AAACATACGT ATGTCACTTT AACTGTAATT GTTGTGCGTG CAAAATGTCA    3420
AATGTGAAAT TAGCTCTCCG GTAAGGGAAG CAAGAGAATG CGGAGAGCAA AGCTCACTTC    3480
CTCAGCCTCA TGTATGTGTA TGTATGTGTA CGACCCTACG ACTCTCAAAG AAAAGTTCAA    3540
AGTGCATGTG TTACAAAACA AAAAACTGTA AATATACATT TAAAGCAAAT GAAACGAAAC    3600
TATACATATA TGTGTATATC CAATTATAGC AATTTACAAA TGCATTGTCA AAATAGTTTT    3660
TATCTTTAAT TATGTATTGA A                                              3681
```

( 2 ) INFORMATION FOR SEQ ID NO:4:

( i ) SEQUENCE CHARACTERISTICS:
        ( A ) LENGTH: 1003 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

-continued

| | | | | | | | | | | | | | | |
|---|---|---|---|---|---|---|---|---|---|---|---|---|---|---|
| Met 1 | Ser | Ser | Ser | Ala 5 | Ala | Ala | Gln | Leu | Thr 10 | Ala | Pro | Pro | Val | Ser 15 | Asn |
| Ser | Asn | Ser | Ser 20 | Ser | Ser | Asn | Asn | Asn 25 | Thr | Thr | Thr | Thr | Ala 30 | Ser | Glu |
| Ser | Asn | Leu | Ile 35 | Ile | Ile | Gln | Asp | Met 40 | Ile | Asp | Leu | Ser 45 | Ala | Asn | His |
| Leu | Glu 50 | Gly | Leu | Arg | Thr | Gln 55 | Cys | Ala | Thr | Ser | Ala 60 | Thr | Leu | Thr | Gln |
| Gln 65 | Glu | Ile | Arg | Cys | Leu 70 | Glu | Ser | Lys | Leu | Val 75 | Arg | Tyr | Phe | Ser | Glu 80 |
| Leu | Leu | Leu | Thr | Lys 85 | Thr | Arg | Leu | Asn | Glu 90 | Arg | Ile | Pro | Ala | Asn 95 | Gly |
| Leu | Leu | Pro | His 100 | His | Gln | Ala | Thr | Gly 105 | Asn | Glu | Leu | Arg | Gln 110 | Trp | Leu |
| Arg | Val | Val 115 | Gly | Leu | Ser | Pro | Glu 120 | Ser | Leu | Asn | Ala | Cys 125 | Leu | Ala | Arg |
| Leu | Thr 130 | Thr | Leu | Glu | Gln | Thr 135 | Leu | Gln | Leu | Ser | Asp 140 | Glu | Glu | Leu | Lys |
| Gln 145 | Leu | Leu | Ala | His | Asn 150 | Ser | Ser | Thr | Gln | Leu 155 | Asp | Glu | Glu | Leu | Arg 160 |
| Arg | Leu | Thr | Lys | Ala 165 | Met | His | Asn | Leu | Arg 170 | Lys | Cys | Met | Glu | Thr 175 | Leu |
| Asp | Ser | Ser | Gly 180 | Ala | Val | Ala | Ser | Asn 185 | Val | Asp | Pro | Glu | Gln 190 | Trp | His |
| Trp | Asp | Ser 195 | Trp | Asp | Arg | Pro | His 200 | Pro | His | His | Met | His 205 | Arg | Gly | Ser |
| Ile | Gly 210 | Asn | Ile | Gly | Leu | Gly 215 | Leu | Ser | Ser | Ala | Ser 220 | Pro | Arg | Ala | His |
| His 225 | Arg | Gln | His | Gln | His 230 | Gln | His | Ala | Asn | Ser 235 | Lys | Pro | Lys | Ile | Val 240 |
| Asn | Asn | Ser | Ala | Ser 245 | Ser | Ser | Arg | Ser | Glu 250 | Gln | Gln | Pro | Leu | Thr 255 | Gly |
| Ser | Gln | Leu | Thr 260 | Leu | Thr | Leu | Thr | Pro 265 | Ser | Pro | Pro | Asn | Ser 270 | Pro | Phe |
| Thr | Pro | Ala 275 | Ser | Gly | Thr | Ala | Ser 280 | Ala | Ser | Gly | Thr | Pro 285 | Gln | Arg | Ser |
| Arg | Ser 290 | Thr | Thr | Thr | Ala | Ala 295 | Gly | Thr | Pro | Pro | Pro 300 | Ala | Lys | Lys | His |
| Gln 305 | Thr | Leu | Leu | Met | His 310 | Asn | Ser | Ser | Ala | Ser 315 | Glu | Thr | Ala | Leu | Ala 320 |
| Glu | Gln | Pro | Pro | Arg 325 | Pro | Pro | Arg | Ser | Arg 330 | Leu | Pro | Thr | Asp | Pro 335 | Ser |
| Pro | Asp | Ser | His 340 | Ser | Ser | Ala | Ser | Ser 345 | Asp | Ile | Phe | Val | Asp 350 | Gly | Gly |
| Gly | Ser | Ile 355 | Asn | Ser | Ser | Asn | Val 360 | Leu | Leu | Val | Pro | Pro 365 | Ser | Pro | Gly |
| Val | Ala 370 | His | Val | Gly | Met | Gly 375 | His | Thr | Ile | Lys | His 380 | Arg | Phe | Ser | Lys |
| Trp 385 | Phe | Gly | Phe | Met | Ala 390 | Thr | Cys | Lys | Leu | Cys 395 | Gln | Lys | Gln | Met | Met 400 |
| Ser | His | Trp | Phe | Lys 405 | Cys | Thr | Asp | Cys | Lys 410 | Tyr | Ile | Cys | His | Lys 415 | Ser |
| Cys | Ala | Pro | His 420 | Val | Pro | Pro | Ser | Cys 425 | Gly | Leu | Pro | Pro | Glu 430 | Tyr | Val |

| | | | | | | | | | | | | | | |
|---|---|---|---|---|---|---|---|---|---|---|---|---|---|---|
|His|Glu|Phe|Arg|Gln|Thr|Gln|Val|Gly|Gly|Arg|Trp|Asp|Pro|Ala|Gln|
| |435| | | |440| | | | |445| | | | |
|His|Ser|Ser|Ser|Lys|Ala|Ser|Pro|Val|Pro|Arg|Lys|Ser|Thr|Leu|Gly|
| |450| | | |455| | | | |460| | | | |
|Lys|Pro|Gln|Leu|Gln|Gln|Pro|Gln|Leu|Gln|His|Gly|Asp|Ser|Ser|Ser|
|465| | | | |470| | | | |475| | | | |480|
|Pro|Ser|Ser|Ser|Cys|Thr|Ser|Ser|Thr|Pro|Ser|Ser|Pro|Ala|Leu|Phe|
| | | | |485| | | | |490| | | | |495| |
|Gln|Gln|Gln|Gln|Leu|Gln|Leu|Ala|Thr|Pro|Ser|Ala|Cys|Gln|Pro|Lys|
| | | |500| | | | |505| | | |510| | | |
|Pro|Ala|Pro|Ala|Ala|Val|Ala|Ala|Ala|Thr|Gln|Gln|Gly|Gln|Gln|
| | |515| | | |520| | | | |525| | | |
|Ser|Gln|Phe|Asn|Phe|Pro|Asn|Val|Thr|Ile|Thr|Ser|Ile|Asn|Ala|Cys|
| |530| | | |535| | | | |540| | | | |
|Asn|Ser|Asn|Ala|Ser|Ala|Ala|Gln|Thr|Leu|Ile|Ser|Asn|Glu|Pro|Gln|
|545| | | | |550| | | | |555| | | | |560|
|Ala|His|Met|Ala|Thr|Thr|Glu|Ser|Thr|Leu|Thr|Asn|Gly|Asn|Asn|Asn|
| | | | |565| | | | |570| | | | |575| |
|Ser|Ser|Ser|Asn|Asn|Gly|Ser|Ser|Ala|Asn|Asn|Ser|Ser|Ser|Ser|
| | | |580| | | | |585| | | |590| | | |
|Ser|Ser|Cys|Ser|Asn|Gly|His|Leu|His|Ser|Leu|Thr|Gly|Ser|Gln|Val|
| | |595| | | |600| | | | |605| | | | |
|Ser|Thr|His|Ser|Ala|Thr|Ser|Gln|Val|Ser|Asn|Val|Ser|Gly|Ser|Ser|
| |610| | | |615| | | | |620| | | | |
|Ser|Ala|Thr|Tyr|Thr|Ser|Ser|Leu|Val|Asn|Ser|Gly|Ser|Phe|Phe|Pro|
|625| | | | |630| | | | |635| | | | |640|
|Arg|Lys|Leu|Ser|Asn|Ala|Gly|Val|Asp|Lys|Arg|Val|Pro|Phe|Thr|Ser|
| | | | |645| | | | |650| | | | |655| |
|Glu|Tyr|Thr|Asp|Thr|His|Lys|Ser|Asn|Asp|Ser|Asp|Lys|Thr|Val|Ser|
| | | |660| | | | |665| | | | |670| | |
|Leu|Ser|Gly|Ser|Ala|Ser|Thr|Asp|Ser|Asp|Arg|Thr|Pro|Val|Arg|Leu|
| | |675| | | | |680| | | | |685| | | |
|Asp|Ser|Thr|Glu|Asp|Gly|Asp|Ser|Gly|Gln|Trp|Arg|Gln|Asn|Ser|Ile|
| |690| | | |695| | | | |700| | | | |
|Ser|Leu|Lys|Glu|Trp|Asp|Ile|Pro|Tyr|Gly|Asp|Leu|His|Leu|Leu|Glu|
|705| | | | |710| | | | |715| | | | |720|
|Arg|Ile|Gly|Gln|Gly|Arg|Phe|Gly|Thr|Val|His|Arg|Ala|Leu|Trp|His|
| | | | |725| | | | |730| | | | |735| |
|Gly|Asp|Val|Ala|Val|Lys|Leu|Leu|Asn|Glu|Asp|Tyr|Leu|Gln|Asp|Glu|
| | | |740| | | | |745| | | | |750| | |
|His|Met|Leu|Glu|Ser|Phe|Arg|Asn|Glu|Val|Ala|Asn|Phe|Lys|Lys|Thr|
| | |755| | | | |760| | | | |765| | | |
|Arg|His|Glu|Asn|Leu|Val|Leu|Phe|Met|Gly|Ala|Cys|Met|Asn|Pro|Pro|
| |770| | | |775| | | | |780| | | | |
|Tyr|Leu|Ala|Ile|Val|Thr|Ala|Leu|Cys|Lys|Gly|Asn|Thr|Leu|Tyr|Thr|
|785| | | | |790| | | | |795| | | | |800|
|Tyr|Ile|His|Gln|Arg|Arg|Glu|Lys|Phe|Ala|Met|Asn|Arg|Thr|Leu|Leu|
| | | | |805| | | | |810| | | | |815| |
|Ile|Ala|Gln|Gln|Ile|Ala|Gln|Gly|Met|Gly|Tyr|Leu|His|Ala|Arg|Asp|
| | | |820| | | | |825| | | | |830| | |
|Ile|Ile|His|Lys|Asp|Leu|Arg|Thr|Lys|Asn|Ile|Phe|Ile|Glu|Asn|Gly|
| | |835| | | | |840| | | | |845| | | |
|Lys|Val|Ile|Ile|Thr|Asp|Phe|Gly|Leu|Phe|Ser|Ser|Thr|Lys|Leu|Leu|

|     |     |     |     |     |     | 850 |     |     |     |     |     | 855 |     |     |     |     |     | 860 |     |     |     |     |     |
|---|---|---|---|---|---|---|---|---|---|---|---|---|---|---|---|---|---|---|---|---|---|---|---|

Tyr Cys Asp Met Gly Leu Gly Val Pro Gln Asn Trp Leu Cys Tyr Leu
865                     870                     875                     880

Ala Pro Glu Leu Ile Arg Ala Leu Gln Pro Cys Lys Pro Pro Gly Glu
                885                     890                     895

Cys Leu Glu Phe Thr Ser Tyr Ser Asp Val Tyr Ser Phe Gly Thr Val
            900                     905                     910

Trp Tyr Glu Leu Ile Cys Gly Glu Phe Thr Phe Lys Asp Gln Pro Ala
        915                     920                     925

Glu Ser Ile Ile Trp Gln Val Gly Arg Gly Met Lys Gln Ser Leu Ala
    930                     935                     940

Asn Leu Gln Ser Gly Arg Asp Val Lys Asp Leu Leu Met Leu Cys Trp
945                     950                     955                     960

Thr Tyr Glu Lys Glu His Arg Pro Asp Phe Ala Arg Leu Leu Ser Leu
                965                     970                     975

Leu Glu His Leu Pro Lys Lys Arg Leu Ala Arg Ser Pro Ser His Pro
            980                     985                     990

Val Asn Leu Ser Arg Ser Ala Glu Ser Val Phe
        995                     1000

( 2 ) INFORMATION FOR SEQ ID NO:5:

( i ) SEQUENCE CHARACTERISTICS:
        ( A ) LENGTH: 4094 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
GAATTCCCTC GGGGCTTTCC TGCCGAGGCG CCCGTGTCCC CGGGCTCCTC GCCTCGGCCC      60
CCAGCGGCCC CGATGCCGAG GCATGGATAG AGCGGCGTTG CGCGCGGCAG CGATGGGCGA     120
GAAAAAGGAG GGCGGCGGCG GGGGCGCCGC GGCGGACGGG GGCGCAGGGG CCGCCGTCAG     180
CCGGGCGCTG CAGCAGTGCG GCCAGCTGCA GAAGCTCATC GATATCTCCA TCGGCAGTCT     240
GCGCGGGCTG CGCACCAAGT GCTCAGTGTC TAACGACCTC ACACAGCAGG AGATCCGGAC     300
CCTAGAGGCA AAGCTGGTGA AATACATTTG CAAGCAGCAG CAGAGCAAGC TTAGTGTGAC     360
CCCAAGCGAC AGGACCGCCG AGCTCAACAG CTACCCACGC TTCAGTGACT GGCTGTACAT     420
CTTCAACGTG AGGCCTGAGG TGGTGCAGGA GATCCCCCAA GAGCTCACAC TGGATGCTCT     480
GCTGGAGATG GACGAGGCCA AGCCAAGGA GATGCTGCGG CGCTGGGGGG CCAGCACGGA     540
GGAGTGCAGC CGCCTACAGC AAGCCCTTAC CTGCCTTCGG AAGGTGACTG GCTGGGAGG     600
GGAGCACAAA ATGGACTCAG GTTGGAGTTC AACAGATGCT CGAGACAGTA GCTTGGGGCC     660
TCCCATGGAC ATGCTTTCCT CGCTGGGCAG AGCGGGTGCC AGCACTCAGG ACCCCGTTC     720
CATCTCCGTG TCCGCCCTGC CTGCCTCAGA CTCTCCGGTC CCCGGCCTCA GTGAGGGCCT     780
CTCGGACTCC TGTATCCCCT TGCACACCAG CGGCCGGCTG ACCCCCGGG CCCTGCACAG     840
CTTCATCACG CCCCCTACCA CACCCCAGCT ACGACGGCAC GCCAAGCTGA AGCCACCAAG     900
GACACCCCCA CCGCCAAGCC GCAAGGTCTT CCAGCTGCTC CCCAGCTTCC CCACACTCAC     960
ACGGAGCAAG TCCCACGAGT CCCAGCTGGG AAACCGAATC GACGACGTCA CCCCGATGAA    1020
GTTTGAACTC CCTCATGGAT CCCCACAGCT GGTACGAAGG GATATCGGGC TCTCGGTGAC    1080
GCACAGGTTC TCCACAAAGT CATGGTTGTC ACAGGTGTGC AACGTGTGCC AGAAGAGCAT    1140
```

```
GATTTTTGGC GTGAAGTGCA AACACTGCAG GTTAAAATGC CATAACAAGT GCACAAAGGA      1200
AGCTCCCGCC TGCAGGATCA CCTTCCTCCC ACTGGCCAGG CTTCGGAGGA CAGAGTCTGT      1260
CCCGTCAGAT ATCAACAACC CAGTGGACAG AGCAGCAGAG CCCCATTTTG GAACCCTTCC      1320
CAAGGCCCTG ACAAAGAAGG AGCACCCTCC AGCCATGAAC CTGGACTCCA GCAGCAACCC      1380
ATCCTCCACC ACGTCCTCCA CACCCTCATC GCCGGCACCT TTCCTGACCT CATCTAATCC      1440
CTCCAGTGCC ACCACGCCTC CCAACCCGTC ACCTGGCCAG CGGGACAGCA GGTTCAGCTT      1500
CCCAGACATT TCAGCCTGTT CTCAGGCAGC CCCGCTGTCC AGCACAGCCG ACAGTACACG      1560
GCTCGACGAC CAGCCCAAAA CAGATGTGCT AGGTGTTCAC GAAGCAGAGG CTGAGGAGCC      1620
TGAGGCTGGC AAGTCAGAGG CAGAGGATGA CGAGGAGGAT GAGGTGGACG ACCTCCCCAG      1680
CTCCCGCCGG CCCTGGAGGG GCCCCATCTC TCGAAAGGCC AGCCAGACCA GCGTTTACCT      1740
GCAAGAGTGG GACATCCCCT TGAACAGGT GGAACTGGGC GAGCCCATTG ACAGGGTCG       1800
CTGGGGCCGG GTGCACCGAG GCCGTTGGCA TGGCGAGGTG GCCATTCGGC TGCTGGAGAT      1860
GGACGGCCAC AATCAGGACC ACCTGAAGCT GTTCAAGAAA GAGGTGATGA ACTACCGGCA      1920
GACGCGGCAT GAGAACGTGG TGCTCTTCAT GGGGGCCTGC ATGAACCCAC CTCACCTGGC      1980
CATTATCACC AGCTTCTGCA AGGGGCGGAC ATTGCATTCA TTCGTGAGGG ACCCCAAGAC      2040
GTCTCTGGAC ATCAATAAGA CTAGGCAGAT CGCCCAGGAG ATCATCAAGG CATGGGTTA      2100
TCTTCATGCA AAAGGCATCG TGCACAAGGA CCTCAAGTCC AAGAATGTCT CTATGACAA      2160
CGGCAAAGTG GTCATCACAG ACTTCGGGCT GTTTGGATC TCGGGTGTGG TCCGAGAGGA      2220
ACGGCGCGAG AACCAACTGA AACTGTCACA TGACTGGCTG TGCTACCTGG CCCCCGAGAT      2280
CGTACGAGAA ATGATCCCGG GGCGGGACGA GGACCAGCTG CCCTTCTCCA AAGCAGCCGA      2340
TGTCTATGCA TTCGGGACTG TGTGGTATGA ACTACAGGCA AGAGACTGGC CCTTTAAGCA      2400
CCAGCCTGCT GAGGCCTTGA TCTGGCAGAT TGGAAGTGGG GAAGGAGTAC GGCGCGTCCT      2460
GGCATCCGTC AGCCTGGGGA AGGAAGTCGG CGAGATCCTG TCTGCCTGCT GGGCTTTCGA      2520
TCTGCAGGAG AGACCCAGCT TCAGCCTGCT GATGGACATG CTGGAGAGGC TGCCCAAGCT      2580
GAACCGGCGG CTCTCCCACC CTGGGCACTT TTGGAAGTCG GCTGACATTA ACAGCAGCAA      2640
AGTCATGCCC CGCTTTGAAA GGTTTGGCCT GGGGACCCTG GAGTCCGGTA ATCCAAAGAT      2700
GTAGCCAGCC CTGCACGTTC ATGCAGAGAG TGTCTTCCTT TCGAAAACAT GATCACGAAA      2760
CATGCAGACC ACCACCTCAA GGAATCAGAA GCATTGCATC CAAGCTGCG GACTGGGAGC      2820
GTGTCTCCTC CCTAAAGGAC GTGCGTGCGT GCGTGCGTGC GTGCGTGCGT GCGTGCGTCA      2880
CCAAGGTGTG TGGAGCTCAG GATCGCAGCC ATACACGCAA CTCCAGATGA TACCACTACC      2940
GCCAGTGTTT ACACAGAGGT TTCTGCCTGG CAAGCTTGGT ATTTTACAGT AGGTGAAGAT      3000
CATTCTGCAG AAGGGTGCTG GCACAGTGGA GCAGCACGGA TGTCCCCAGC CCCCGTTCTG      3060
GAAGACCCTA CAGCTGTGAG AGGCCCAGGG TTGAGCCAGA TGAAAGAAAA GCTGCGTGGG      3120
TGTGGGCTGT ACCCGGAAAA GGGCAGGTGG CAGGAGGTTT GCCTTGGCCT GTGCTTGGGC      3180
CGAGAACCAC ACTAAGGAGC AGCAGCCTGA GTTAGGAATC TATCTGGATT ACGGGGATCA      3240
GAGTTCCTGG AGAGTGGACT CAGTTTCTGC TCTGATCCAG GCCTGTTGTG CTTTTTTTT      3300
TTCCCCCTTA AAAAAAAAA AGTACAGACA GAATCTCAGC GGCTTCTAGA CTGATCTGAT      3360
GGATCTTAGC CCGGCTTCTA CTGCGGGGGG GAGGGGGGA GGGATAGCCA CATATCTGTG      3420
GAGACACCCA CTTCTTTATC TGAGGCCTCC AGGTAGGCAC AAAGGCTGTG GAACTCAGCC      3480
TCTATCATCA GACACCCCCC CCCAATGCCT CATTGACCCC CTTCCCCCAG AGCCAAGGGC      3540
```

```
TAGCCCATCG GGTGTGTGTA CAGTAAGTTC TTGGTGAAGG AGAACAGGGA CGTTGGCAGA      3600

AGCAGTTTGC AGTGGCCCTA GCATCTTAAA ACCCATTGTC TGTCACACCA GAAGGTTCTA      3660

GACCTACCAC CACTTCCCTT CCCCATCTCA TGGAAACCTT TTAGCCCATT CTGACCCCTG      3720

TGTGTGCTCT GAGCTCAGAT CGGGTTATGA GACCGCCCAG GCACATCAGT CAGGGAGGCT      3780

CTGATGTGAG CCGCAGACCT CTGTGTTCAT TCCTATGAGC TGGAGGGGCT GGACTGGGTG      3840

GGGTCAGATG TGCTTGGCAG GAACTGTCAG CTGCTGAGCA GGGTGGTCCC TGAGCGGAGG      3900

ATAAGCAGCA TCAGACTCCA CAACCAGAGG AAGAAAGAAA TGGGGATGGA GCGGAGACCC      3960

ACGGGCTGAG TCCCGCTGTG GAGTGGCCTT GCAGCTCCCT CTCAGTTAAA ACTCCCAGTA      4020

AAGCCACAGT TCTCCGAGCA CCCAAGTCTG CTCCAGCCGT CTCTTAAAAC AGGCCACTCT      4080

CTGAGAAGGA ATTC                                                        4094
```

( 2 ) INFORMATION FOR SEQ ID NO:6:

( i ) SEQUENCE CHARACTERISTICS:
        ( A ) LENGTH: 873 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:6:

```
Met Asp Arg Ala Ala Leu Arg Ala Ala Ala Met Gly Glu Lys Lys Glu
 1               5                  10                  15

Gly Gly Gly Gly Gly Ala Ala Ala Asp Gly Gly Ala Gly Ala Ala Val
                20                  25                  30

Ser Arg Ala Leu Gln Gln Cys Gly Gln Leu Gln Lys Leu Ile Asp Ile
            35                  40                  45

Ser Ile Gly Ser Leu Arg Gly Leu Arg Thr Lys Cys Ser Val Ser Asn
50                  55                  60

Asp Leu Thr Gln Gln Glu Ile Arg Thr Leu Glu Ala Lys Leu Val Lys
65                  70                  75                  80

Tyr Ile Cys Lys Gln Gln Gln Ser Lys Leu Ser Val Thr Pro Ser Asp
                85                  90                  95

Arg Thr Ala Glu Leu Asn Ser Tyr Pro Arg Phe Ser Asp Trp Leu Tyr
            100                 105                 110

Ile Phe Asn Val Arg Pro Glu Val Val Gln Glu Ile Pro Gln Glu Leu
        115                 120                 125

Thr Leu Asp Ala Leu Leu Glu Met Asp Glu Ala Lys Ala Lys Glu Met
    130                 135                 140

Leu Arg Arg Trp Gly Ala Ser Thr Glu Glu Cys Ser Arg Leu Gln Gln
145                 150                 155                 160

Ala Leu Thr Cys Leu Arg Lys Val Thr Gly Leu Gly Gly Glu His Lys
                165                 170                 175

Met Asp Ser Gly Trp Ser Ser Thr Asp Ala Arg Asp Ser Ser Leu Gly
            180                 185                 190

Pro Pro Met Asp Met Leu Ser Ser Leu Gly Arg Ala Gly Ala Ser Thr
        195                 200                 205

Gln Gly Pro Arg Ser Ile Ser Val Ser Ala Leu Pro Ala Ser Asp Ser
    210                 215                 220

Pro Val Pro Gly Leu Ser Glu Gly Leu Ser Asp Ser Cys Ile Pro Leu
225                 230                 235                 240

His Thr Ser Gly Arg Leu Thr Pro Arg Ala Leu His Ser Phe Ile Thr
                245                 250                 255
```

```
Pro  Pro  Thr  Thr  Pro  Gln  Leu  Arg  Arg  His  Ala  Lys  Leu  Lys  Pro  Pro
          260                 265                     270

Arg  Thr  Pro  Pro  Pro  Ser  Arg  Lys  Val  Phe  Gln  Leu  Leu  Pro  Ser
          275                 280                     285

Phe  Pro  Thr  Leu  Thr  Arg  Ser  Lys  Ser  His  Glu  Ser  Gln  Leu  Gly  Asn
          290                 295                     300

Arg  Ile  Asp  Asp  Val  Thr  Pro  Met  Lys  Phe  Glu  Leu  Pro  His  Gly  Ser
305                      310                 315                           320

Pro  Gln  Leu  Val  Arg  Arg  Asp  Ile  Gly  Leu  Ser  Val  Thr  His  Arg  Phe
                    325                 330                     335

Ser  Thr  Lys  Ser  Trp  Leu  Ser  Gln  Val  Cys  Asn  Val  Cys  Gln  Lys  Ser
               340                 345                     350

Met  Ile  Phe  Gly  Val  Lys  Cys  Lys  His  Cys  Arg  Leu  Lys  Cys  His  Asn
               355                 360                     365

Lys  Cys  Thr  Lys  Glu  Ala  Pro  Ala  Cys  Arg  Ile  Thr  Phe  Leu  Pro  Leu
     370                      375                     380

Ala  Arg  Leu  Arg  Arg  Thr  Glu  Ser  Val  Pro  Ser  Asp  Ile  Asn  Asn  Pro
385                      390                     395                      400

Val  Asp  Arg  Ala  Ala  Glu  Pro  His  Phe  Gly  Thr  Leu  Pro  Lys  Ala  Leu
                    405                 410                           415

Thr  Lys  Lys  Glu  His  Pro  Pro  Ala  Met  Asn  Leu  Asp  Ser  Ser  Ser  Asn
                    420                 425                      430

Pro  Ser  Ser  Thr  Thr  Ser  Ser  Thr  Pro  Ser  Ser  Pro  Ala  Pro  Phe  Leu
          435                 440                     445

Thr  Ser  Ser  Asn  Pro  Ser  Ser  Ala  Thr  Thr  Pro  Pro  Asn  Pro  Ser  Pro
     450                      455                     460

Gly  Gln  Arg  Asp  Ser  Arg  Phe  Ser  Phe  Pro  Asp  Ile  Ser  Ala  Cys  Ser
465                      470                 475                           480

Gln  Ala  Ala  Pro  Leu  Ser  Ser  Thr  Ala  Asp  Ser  Thr  Arg  Leu  Asp  Asp
               485                 490                           495

Gln  Pro  Lys  Thr  Asp  Val  Leu  Gly  Val  His  Glu  Ala  Glu  Ala  Glu  Glu
               500                 505                     510

Pro  Glu  Ala  Gly  Lys  Ser  Glu  Ala  Glu  Asp  Asp  Glu  Asp  Glu  Val
          515                 520                     525

Asp  Asp  Leu  Pro  Ser  Ser  Arg  Arg  Pro  Trp  Arg  Gly  Pro  Ile  Ser  Arg
     530                 535                     540

Lys  Ala  Ser  Gln  Thr  Ser  Val  Tyr  Leu  Gln  Glu  Trp  Asp  Ile  Pro  Phe
545                      550                     555                      560

Glu  Gln  Val  Glu  Leu  Gly  Glu  Pro  Ile  Gly  Gln  Gly  Arg  Trp  Gly  Arg
                    565                 570                     575

Val  His  Arg  Gly  Arg  Trp  His  Gly  Glu  Val  Ala  Ile  Arg  Leu  Leu  Glu
               580                 585                     590

Met  Asp  Gly  His  Asn  Gln  Asp  His  Leu  Lys  Leu  Phe  Lys  Lys  Glu  Val
          595                 600                     605

Met  Asn  Tyr  Arg  Gln  Thr  Arg  His  Glu  Asn  Val  Val  Leu  Phe  Met  Gly
     610                      615                     620

Ala  Cys  Met  Asn  Pro  Pro  His  Leu  Ala  Ile  Ile  Thr  Ser  Phe  Cys  Lys
625                      630                     635                      640

Gly  Arg  Thr  Leu  His  Ser  Phe  Val  Arg  Asp  Pro  Lys  Thr  Ser  Leu  Asp
                    645                 650                           655

Ile  Asn  Lys  Thr  Arg  Gln  Ile  Ala  Gln  Glu  Ile  Ile  Lys  Gly  Met  Gly
               660                 665                     670

Tyr  Leu  His  Ala  Lys  Gly  Ile  Val  His  Lys  Asp  Leu  Lys  Ser  Lys  Asn
```

|     | 675 |     |     |     |     | 680 |     |     |     |     | 685 |     |     |     |
|-----|-----|-----|-----|-----|-----|-----|-----|-----|-----|-----|-----|-----|-----|-----|
| Val | Phe 690 | Tyr | Asp | Asn | Gly | Lys 695 | Val | Val | Ile | Thr | Asp 700 | Phe | Gly | Leu | Phe |
| Gly 705 | Ile | Ser | Gly | Val | Val 710 | Arg | Glu | Glu | Arg | Glu 715 | Asn | Gln | Leu | Lys 720 |
| Leu | Ser | His | Asp | Trp 725 | Leu | Cys | Tyr | Leu | Ala 730 | Pro | Glu | Ile | Val | Arg 735 | Glu |
| Met | Ile | Pro | Gly 740 | Arg | Asp | Glu | Asp | Gln 745 | Leu | Pro | Phe | Ser | Lys 750 | Ala | Ala |
| Asp | Val | Tyr 755 | Ala | Phe | Gly | Thr | Val 760 | Trp | Tyr | Glu | Leu | Gln 765 | Ala | Arg | Asp |
| Trp | Pro 770 | Phe | Lys | His | Gln | Pro 775 | Ala | Glu | Ala | Leu | Ile 780 | Trp | Gln | Ile | Gly |
| Ser 785 | Gly | Glu | Gly | Val | Arg 790 | Arg | Val | Leu | Ala | Ser 795 | Val | Ser | Leu | Gly | Lys 800 |
| Glu | Val | Gly | Glu | Ile 805 | Leu | Ser | Ala | Cys | Trp 810 | Ala | Phe | Asp | Leu | Gln 815 | Glu |
| Arg | Pro | Ser | Phe 820 | Ser | Leu | Leu | Met | Asp 825 | Met | Leu | Glu | Arg | Leu 830 | Pro | Lys |
| Leu | Asn | Arg 835 | Arg | Leu | Ser | His | Pro 840 | Gly | His | Phe | Trp | Lys 845 | Ser | Ala | Asp |
| Ile | Asn 850 | Ser | Ser | Lys | Val | Met 855 | Pro | Arg | Phe | Glu | Arg 860 | Phe | Gly | Leu | Gly |
| Thr 865 | Leu | Glu | Ser | Gly | Asn 870 | Pro | Lys | Met |     |     |     |     |     |     |     |

( 2 ) INFORMATION FOR SEQ ID NO:7:

( i ) SEQUENCE CHARACTERISTICS:
        ( A ) LENGTH: 2846 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| | | | | | | |
|---|---|---|---|---|---|---|
| AGAGCAGCGC | TGCGCTCGGC | CGCGTTGGGA | GAGAAGAAGG | AGGGCGGTGG | CGGGGGTGAC | 60 |
| GCGGCTATCG | CGGAGGGAGG | TGCAGGGGCC | GCGGCCAGCC | GGACACTGCA | GCAGTGCGGG | 120 |
| CAGCTGCAGA | AGCTCATCGA | CATCTCCATC | GGCAGCCTGC | GCGGGCTGCG | CACCAAGTGC | 180 |
| GTGGTGTCCA | ACGACCTCAC | CCAGCAGGAG | ATACGGACCC | TGGAGGCGAA | GCTGGTCCGT | 240 |
| TACATTTGTA | AGCAGAGGCA | GTGCAAGCTG | AGCGTGGCTC | CCGGTGAGAG | GACCCCAGAG | 300 |
| CTCAACAGCT | ACCCCGCTT | CAGCGACTGG | CTGTACACTT | TCAACGTGAG | GCCGGAGGTG | 360 |
| GTGCAGGAGA | TCCCCCGAGA | CCTCACGCTG | GATGCCCTGC | TGGAGATGAA | TGAGGCCAAG | 420 |
| GTGAAGGAGA | CGCTGCGGCG | CTGTGGGGCC | AGCGGGGATG | AGTGTGGCCG | TCTGCAGTAT | 480 |
| GCCCTCACCT | GCCTGCGGAA | GGTGACAGGC | CTGGGAGGGG | AGCACAAGGA | GGACTCCAGT | 540 |
| TGGAGTTCAT | TGGATGCGCG | GCGGGAAAGT | GGCTCAGGGC | CTTCCACGGA | CACCCTCTCA | 600 |
| GCAGCCAGCC | TGCCCTGGCC | CCCAGGGAGC | TCCCAGCTGG | GCAGAGCAGG | CAACAGCGCC | 660 |
| CAGGGCCCAC | GCTCCATCTC | CGTGTCAGCT | CTTCCCGCCT | CAGACTCCCC | CACCCCCAGC | 720 |
| TTCAGTGAGG | GCCTCTCAGA | CACCTGTATT | CCCCTGCACG | CCAGCGGCCG | GCTGACCCCC | 780 |
| CGTGCCCTGC | ACAGCTTCAT | CACCCCGCCC | ACCACACCCC | AGCTGCGACG | GCACACCAAG | 840 |
| CTGAAGCCAC | CACGGACGCC | CCCCCACCC | AGCCGCAAGG | TCTTCCAGCT | GCTGCCCAGC | 900 |

```
TTCCCCACAC TCACCCGGAG CAAGTCCCAT GAGTCTCAGC TGGGGAACCG CATTGATGAC      960
GTCTCCTCGA TGAGGTTTGA TCTCTCGCAT GGATCCCCAC AGATGGTACG GAGGGATATC     1020
GGGCTGTCGG TGACGCACAG GTTCTCCACC AAGTCCTGGC TGTCGCAGGT CTGCCACGTG     1080
TGCCAGAAGA GCATGATATT TGGAGTGAAG TGCAAGCATT GCAGGTTGAA GTGTCACAAC     1140
AAATGTACCA AGAAGCCCC  TGCCTGTAGA ATATCCTTCC TGCCACTAAC TCGGCTTCGG     1200
AGGACAGAAT CTGTCCCCTC GGACATCAAC AACCCGGTGG ACAGAGCAGC CGAACCCCAT     1260
TTTGGAACCC TCCCCAAAGC ACTGACAAAG AAGGAGCACC CTCCGGCCAT GAATCACCTG     1320
GACTCCAGCA GCAACCCTTC CTCCACCACC TCCTCCACAC CCTCCTCACC GGCGCCCTTC     1380
CCGACATCAT CCAACCCATC CAGCGCCACC ACGCCCCCA  ACCCCTCACC TGGCCAGCGG     1440
GACAGCAGGT TCAACTTCCC AGCTGCCTAC TTCATTCATC ATAGACAGCA GTTTATCTTT     1500
CCAGACATTT CAGCCTTTGC ACACGCAGCC CCGCTCCCTG AAGCTGCCGA CGGTACCCGG     1560
CTCGATGACC AGCCGAAAGC AGATGTGTTG GAAGCTCACG AAGCGGAGGC TGAGGAGCCA     1620
GAGGCTGGCA AGTCAGAGGC AGAAGACGAT GAGGACGAGG TGGACGACTT GCCGAGCTCT     1680
CGCCGGCCCT GGCGGGGCCC CATCTCTCGC AAGGCCAGCC AGACCAGCGT GTACCTGCAG     1740
GAGTGGACA  TCCCCTTCGA GCAGGTAGAG CTGGGCGAGC CCATCGGGCA GGGCCGCTGG     1800
GGCCGGGTGC ACCGCGGCCG CTGGCATGGC GAGGTGGCCA TTCGCCTGCT GGAGATGGAC     1860
GGCCACAACC AGGACCACCT GAAGCTCTTC AAGAAAGAGG TGATGAACTA CCGGCAGACG     1920
CGGCATGAGA ACGTGGTGCT CTTCATGGGG GCCTGCATGA ACCCGCCCCA CCTGGCCATT     1980
ATCACCAGCT TCTGCAAGGG GCGGACGTTG CACTCGTTTG TGAGGGACCC CAAGACGTCT     2040
CTGGACATCA ACAAGACGAG GCAAATCGCT CAGGAGATCA TCAAGGGCAT GGGATATCTT     2100
CATGCCAAGG GCATCGTACA CAAAGATCTC AAATCTAAGA ACGTCTTCTA TGACAACGGC     2160
AAGGTGGTCA TCACAGACTT CGGGCTGTTT GGGATCTCAG GCGTGGTCCG AGAGGGACGG     2220
CGTGAGAACC AGCTAAAGCT GTCCCACGAC TGGCTGTGCT ATCTGGCCCC TGAGATTGTA     2280
CGCGAGATGA CCCCCGGGAA GGACGAGGAT CAGCTGCCAT TCTCCAAAGC TGCTGATGTC     2340
TATGCATTTG GGACTGTTTG GTATGAGCTG CAAGCAAGAG ACTGGCCCTT GAAGAACCAG     2400
GCTGCAGAGG CATCCATCTG GCAGATTGGA AGCGGGGAAG GAATGAAGCG TGTCCTGACT     2460
TCTGTCAGCT TGGGGAAGGA AGTCAGTGAG ATCCTGTCGG CCTGCTGGGC TTTCGACCTG     2520
CAGGAGAGAC CCAGCTTCAG CCTGCTGATG GACATGCTGG AGAAACTTCC CAAGCTGAAC     2580
CGGCGGCTCT CCCACCCTGG ACACTTCTGG AAGTCAGCTG AGTTGTAGGC CTGGCTGCCT     2640
TGCATGCACC AGGGGCTTTC TTCCTCCTAA TCAACAACTC AGCACCGTGA CTTCTGCTAA     2700
AATGCAAAAT GAGATGCGGG CACTAACCCA GGGGATGCCA CCTCTGCTGC TCCAGTCGTC     2760
TCTCTCGAGG CTACTTCTTT TGCTTTGTTT TAAAAACTGG CCCTCTGCCC TCTCCACGTG     2820
GCCTGCATAT GCCCAAGCCG GAATTC                                         2846
```

( 2 ) INFORMATION FOR SEQ ID NO:8:

( i ) SEQUENCE CHARACTERISTICS:
        ( A ) LENGTH: 875 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:8:

```
Arg Ala Ala Leu Arg Ser Ala Ala Leu Gly Glu Lys Lys Glu Gly Gly
1               5                   10                  15

Gly Gly Gly Asp Ala Ala Ile Ala Glu Gly Gly Ala Gly Ala Ala Ala
            20              25              30

Ser Arg Thr Leu Gln Gln Cys Gly Gln Leu Gln Lys Leu Ile Asp Ile
        35              40                  45

Ser Ile Gly Ser Leu Arg Gly Leu Arg Thr Lys Cys Val Val Ser Asn
    50              55                  60

Asp Leu Thr Gln Gln Glu Ile Arg Thr Leu Glu Ala Lys Leu Val Arg
65                  70              75                      80

Tyr Ile Cys Lys Gln Arg Gln Cys Lys Leu Ser Val Ala Pro Gly Glu
                85              90                      95

Arg Thr Pro Glu Leu Asn Ser Tyr Pro Arg Phe Ser Asp Trp Leu Tyr
            100             105             110

Thr Phe Asn Val Arg Pro Glu Val Val Gln Glu Ile Pro Arg Asp Leu
        115             120             125

Thr Leu Asp Ala Leu Leu Glu Met Asn Glu Ala Lys Val Lys Glu Thr
130             135             140

Leu Arg Arg Cys Gly Ala Ser Gly Asp Glu Cys Gly Arg Leu Gln Tyr
145             150             155                     160

Ala Leu Thr Cys Leu Arg Lys Val Thr Gly Leu Gly Gly Glu His Lys
                165             170                     175

Glu Asp Ser Ser Trp Ser Ser Leu Asp Ala Arg Arg Glu Ser Gly Ser
            180             185             190

Gly Pro Ser Thr Asp Thr Leu Ser Ala Ala Ser Leu Pro Trp Pro Pro
            195             200             205

Gly Ser Ser Gln Leu Gly Arg Ala Gly Asn Ser Ala Gln Gly Pro Arg
210             215             220

Ser Ile Ser Val Ser Ala Leu Pro Ala Ser Asp Ser Pro Thr Pro Ser
225             230             235             240

Phe Ser Glu Gly Leu Ser Asp Thr Cys Ile Pro Leu His Ala Ser Gly
            245             250             255

Arg Leu Thr Pro Arg Ala Leu His Ser Phe Ile Thr Pro Thr Thr Thr
            260             265             270

Pro Gln Leu Arg Arg His Thr Lys Leu Lys Pro Pro Arg Thr Pro Pro
        275             280             285

Pro Pro Ser Arg Lys Val Phe Gln Leu Leu Pro Ser Phe Pro Thr Leu
        290             295             300

Thr Arg Ser Lys Ser His Glu Ser Gln Leu Gly Asn Arg Ile Asp Asp
305             310             315             320

Val Ser Ser Met Arg Phe Asp Leu Ser His Gly Ser Pro Gln Met Val
            325             330             335

Arg Arg Asp Ile Gly Leu Ser Val Thr His Arg Phe Ser Thr Lys Ser
            340             345             350

Trp Leu Ser Gln Val Cys His Val Cys Gln Lys Ser Met Ile Phe Gly
        355             360             365

Val Lys Cys Lys His Cys Arg Leu Lys Cys His Asn Lys Cys Thr Lys
370                 375             380

Glu Ala Pro Ala Cys Arg Ile Ser Phe Leu Pro Leu Thr Arg Leu Arg
385             390             395             400

Arg Thr Glu Ser Val Pro Ser Asp Ile Asn Asn Pro Val Asp Arg Ala
            405             410             415

Ala Glu Pro His Phe Gly Thr Leu Pro Lys Ala Leu Thr Lys Lys Glu
            420             425             430
```

-continued

| His | Pro | Pro<br>435 | Ala | Met | Asn | His | Leu<br>440 | Asp | Ser | Ser | Ser | Asn<br>445 | Pro | Ser | Ser |
|---|---|---|---|---|---|---|---|---|---|---|---|---|---|---|---|
| Thr | Thr<br>450 | Ser | Ser | Thr | Pro | Ser<br>455 | Ser | Pro | Ala | Pro | Phe<br>460 | Pro | Thr | Ser | Ser |
| Asn<br>465 | Pro | Ser | Ser | Ala | Thr<br>470 | Thr | Pro | Pro | Asn | Pro<br>475 | Ser | Pro | Gly | Gln | Arg<br>480 |
| Asp | Ser | Arg | Phe | Asn<br>485 | Phe | Pro | Ala | Ala | Tyr<br>490 | Phe | Ile | His | His | Arg<br>495 | Gln |
| Gln | Phe | Ile | Phe<br>500 | Pro | Asp | Ile | Ser | Ala<br>505 | Phe | Ala | His | Ala | Ala<br>510 | Pro | Leu |
| Pro | Glu | Ala<br>515 | Ala | Asp | Gly | Thr | Arg<br>520 | Leu | Asp | Asp | Gln | Pro<br>525 | Lys | Ala | Asp |
| Val | Leu<br>530 | Glu | Ala | His | Glu | Ala<br>535 | Glu | Ala | Glu | Glu | Pro<br>540 | Glu | Ala | Gly | Lys |
| Ser<br>545 | Glu | Ala | Glu | Asp | Asp<br>550 | Glu | Asp | Glu | Val | Asp<br>555 | Asp | Leu | Pro | Ser | Ser<br>560 |
| Arg | Arg | Pro | Trp | Arg<br>565 | Gly | Pro | Ile | Ser | Arg<br>570 | Lys | Ala | Ser | Gln | Thr<br>575 | Ser |
| Val | Tyr | Leu | Gln<br>580 | Glu | Trp | Asp | Ile | Pro<br>585 | Phe | Glu | Gln | Val | Glu<br>590 | Leu | Gly |
| Glu | Pro | Ile<br>595 | Gly | Gln | Gly | Arg | Trp<br>600 | Gly | Arg | Val | His | Arg<br>605 | Gly | Arg | Trp |
| His | Gly<br>610 | Glu | Val | Ala | Ile | Arg<br>615 | Leu | Leu | Glu | Met | Asp<br>620 | Gly | His | Asn | Gln |
| Asp<br>625 | His | Leu | Lys | Leu | Phe<br>630 | Lys | Lys | Glu | Val | Met<br>635 | Asn | Tyr | Arg | Gln | Thr<br>640 |
| Arg | His | Glu | Asn | Val<br>645 | Val | Leu | Phe | Met | Gly<br>650 | Ala | Cys | Met | Asn | Pro<br>655 | Pro |
| His | Leu | Ala | Ile<br>660 | Ile | Thr | Ser | Phe | Cys<br>665 | Lys | Gly | Arg | Thr | Leu<br>670 | His | Ser |
| Phe | Val | Arg<br>675 | Asp | Pro | Lys | Thr | Ser<br>680 | Leu | Asp | Ile | Asn | Lys<br>685 | Thr | Arg | Gln |
| Ile | Ala<br>690 | Gln | Glu | Ile | Ile | Lys<br>695 | Gly | Met | Gly | Tyr | Leu<br>700 | His | Ala | Lys | Gly |
| Ile<br>705 | Val | His | Lys | Asp | Leu<br>710 | Lys | Ser | Lys | Asn | Val<br>715 | Phe | Tyr | Asp | Asn | Gly<br>720 |
| Lys | Val | Val | Ile | Thr<br>725 | Asp | Phe | Gly | Leu | Phe<br>730 | Gly | Ile | Ser | Gly | Val<br>735 | Val |
| Arg | Glu | Gly | Arg | Arg<br>740 | Glu | Asn | Gln | Leu | Lys<br>745 | Leu | Ser | His | Asp<br>750 | Trp | Leu |
| Cys | Tyr | Leu<br>755 | Ala | Pro | Glu | Ile | Val<br>760 | Arg | Glu | Met | Thr | Pro<br>765 | Gly | Lys | Asp |
| Glu | Asp<br>770 | Gln | Leu | Pro | Phe | Ser<br>775 | Lys | Ala | Ala | Asp | Val<br>780 | Tyr | Ala | Phe | Gly |
| Thr<br>785 | Val | Trp | Tyr | Glu | Leu<br>790 | Gln | Ala | Arg | Asp | Trp<br>795 | Pro | Leu | Lys | Asn | Gln<br>800 |
| Ala | Ala | Glu | Ala | Ser<br>805 | Ile | Trp | Gln | Ile | Gly<br>810 | Ser | Gly | Glu | Gly<br>815 | Met | Lys |
| Arg | Val | Leu<br>820 | Thr | Ser | Val | Ser | Leu<br>825 | Gly | Lys | Glu | Val | Ser<br>830 | Glu | Ile | Leu |
| Ser | Ala | Cys<br>835 | Trp | Ala | Phe | Asp | Leu<br>840 | Gln | Glu | Arg | Pro | Ser<br>845 | Phe | Ser | Leu |
| Leu | Met | Asp | Met | Leu | Glu | Lys | Leu | Pro | Lys | Leu | Asn | Arg | Arg | Leu | Ser |

|  | 850 |  |  | 855 |  |  |  | 860 |  |
|---|---|---|---|---|---|---|---|---|---|
| His | Pro | Gly | His | Phe | Trp | Lys | Ser | Ala | Glu | Leu |
| 865 |  |  |  | 870 |  |  |  |  | 875 |

( 2 ) INFORMATION FOR SEQ ID NO:9:

( i ) SEQUENCE CHARACTERISTICS:
      ( A ) LENGTH: 2126 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:9:

```
GAATTCCGGC ACACATCAGC ACTCACACAG CACACAGCAC ACACACAGCA CACATCAGCG      60
CACACACAGC ACAGCTTCAT CACCCCGCCC ACCACACCCC AGCTGCGACG GCACACCAAG     120
CTGAAGCCAC CACGGACGCC CCCCCCACCC AGCCGCAAGG TCTTCCAGCT GCTGCCCAGC     180
TTCCCCACAC TCACCCGGAG CAAGTCCCAT GAGTCTCAGC TGGGGAACCG CATTGATGAC     240
GTCTCCTCGA TGAGGTTTGA TCTCTCGCAT GGATCCCCAC AGATGGTACG GAGGGATATC     300
GGGCTGTCGG TGACGCACAG GTTCTCCACC AAGTCCTGGC TGTCGCAGGT CTGCCACGTG     360
TGCCAGAAGA GCATGATATT TGGAGTGAAG TGCAAGCATT GCAGGTTGAA GTGTCACAAC     420
AAATGTACCA AGAAGCCCCC TGCCTGTAGA ATATCCTTCC TGCCACTAAC TCGGCTTCGG     480
AGGACAGAAT CTGTCCCCTC GGACATCAAC AACCCGGTGG ACAGAGCAGC CGAACCCCAT     540
TTTGGAACCC TCCCCAAAGC ACTGACAAAG AAGGAGCACC CTCCGGCCAT GAATCACCTG     600
GACTCCAGCA GCAACCCTTC CTCCACCACC TCCTCCACAC CCTCCTCACC GGCGCCCTTC     660
CCGACATCAT CCAACCCATC CAGCGCCACC ACGCCCCCA ACCCCTCACC TGGCCAGCGG     720
GACAGCAGGT TCAACTTCCC AGCTGCCTAC TTCATTCATC ATAGACAGCA GTTTATCTTT     780
CCAGACATTT CAGCCTTTGC ACACGCAGCC CCGCTCCCTG AAGCTGCCGA CGGTACCCGG     840
CTCGATGACC AGCCGAAAGC AGATGTGTTG GAAGCTCACG AAGCGGAGGC TGAGGAGCCA     900
GAGGCTGGCA AGTCAGAGGC AGAAGACGAT GAGGACGAGG TGGACGACTT GCCGAGCTCT     960
CGCCGGCCCT GGCGGGGCCC CATCTCTCGC AAGGCCAGCC AGACCAGCGT GTACCTGCAG    1020
GAGTGGGACA TCCCCTTCGA GCAGGTAGAG CTGGGCGAGC CCATCGGGCA GGGCCGCTGG    1080
GGCCGGGTGC ACCGCGGCCG CTGGCATGGC GAGGTGGCCA TTCGCCTGCT GGAGATGGAC    1140
GGCCACAACC AGGACCACCT GAAGCTCTTC AAGAAAGAGG TGATGAACTA CCGGCAGACG    1200
CGGCATGAGA ACGTGGTGCT CTTCATGGGG GCCTGCATGA ACCCGCCCCA CCTGGCCATT    1260
ATCACCAGCT TCTGCAAGGG GCGGACGTTG CACTCGTTTG TGAGGGACCC CAAGACGTCT    1320
CTGGACATCA ACAAGACGAG GCAAATCGCT CAGGAGATCA TCAAGGGCAT GGGATATCTT    1380
CATGCCAAGG GCATCGTACA CAAAGATCTC AAATCTAAGA ACGTCTTCTA TGACAACGGC    1440
AAGGTGGTCA TCACAGACTT CGGGCTGTTT GGGATCTCAG GCGTGGTCCG AGAGGGACGG    1500
CGTGAGAACC AGCTAAAGCT GTCCACGAC TGGCTGTGCT ATCTGGCCCC TGAGATTGTA    1560
CGCGAGATGA CCCCCGGGAA GGACGAGGAT CAGCTGCCAT TCTCCAAAGC TGCTGATGTC    1620
TATGCATTTG GGACTGTTTG GTATGAGCTG CAAGCAAGAG ACTGGCCCTT GAAGAACCAG    1680
GCTGCAGAGG CATCCATCTG GCAGATTGGA AGCGGGGAAG GAATGAAGCG TGTCCTGACT    1740
TCTGTCAGCT TGGGGAAGGA AGTCAGTGAG ATCCTGTCGG CCTGCTGGGC TTTCGACCTG    1800
CAGGAGAGAC CCAGCTTCAG CCTGCTGATG GACATGCTGG AGAAACTTCC CAAGCTGAAC    1860
```

-continued

```
CGGCGGCTCT CCCACCCTGG ACACTTCTGG AAGTCAGCTG AGTTGTAGGC CTGGCTGCCT    1920

TGCATGCACC AGGGGCTTTC TTCCTCCTAA TCAACAACTC AGCACCGTGA CTTCTGCTAA    1980

AATGCAAAAT GAGATGCGGG CACTAACCCA GGGGATGCCA CCTCTGCTGC TCCAGTCGTC    2040

TCTCTCGAGG CTACTTCTTT TGCTTTGTTT TAAAAACTGG CCCTCTGCCC TCTCCACGTG    2100

GCCTGCATAT GCCCAAGCCG GAATTC                                         2126
```

( 2 ) INFORMATION FOR SEQ ID NO:10:

( i ) SEQUENCE CHARACTERISTICS:
        ( A ) LENGTH: 635 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:10:

```
Glu Phe Arg His Thr Ser Ala Leu Thr Gln His Thr Ala His Thr Gln
 1               5                  10                 15

His Thr Ser Ala His Thr Gln His Ser Phe Ile Thr Pro Pro Thr Thr
             20                  25                 30

Pro Gln Leu Arg Arg His Thr Lys Leu Lys Pro Pro Arg Thr Pro Pro
         35                  40                 45

Pro Pro Ser Arg Lys Val Phe Gln Leu Leu Pro Ser Phe Pro Thr Leu
     50                  55                 60

Thr Arg Ser Lys Ser His Glu Ser Gln Leu Gly Asn Arg Ile Asp Asp
 65                  70                  75                 80

Val Ser Ser Met Arg Phe Asp Leu Ser His Gly Ser Pro Gln Met Val
                 85                  90                 95

Arg Arg Asp Ile Gly Leu Ser Val Thr His Arg Phe Ser Thr Lys Ser
            100                 105                110

Trp Leu Ser Gln Val Cys His Val Cys Gln Lys Ser Met Ile Phe Gly
        115                 120                125

Val Lys Cys Lys His Cys Arg Leu Lys Cys His Asn Lys Cys Thr Lys
    130                 135                 140

Glu Ala Pro Ala Cys Arg Ile Ser Phe Leu Pro Leu Thr Arg Leu Arg
145                 150                 155                160

Arg Thr Glu Ser Val Pro Ser Asp Ile Asn Asn Pro Val Asp Arg Ala
                165                 170                 175

Ala Glu Pro His Phe Gly Thr Leu Pro Lys Ala Leu Thr Lys Lys Glu
            180                 185                 190

His Pro Pro Ala Met Asn His Leu Asp Ser Ser Ser Asn Pro Ser Ser
        195                 200                 205

Thr Thr Ser Ser Thr Pro Ser Ser Pro Ala Pro Phe Pro Thr Ser Ser
210                 215                 220

Asn Pro Ser Ser Ala Thr Thr Pro Pro Asn Pro Ser Pro Gly Gln Arg
225                 230                 235                 240

Asp Ser Arg Phe Asn Phe Pro Ala Ala Tyr Phe Ile His His Arg Gln
                245                 250                 255

Gln Phe Ile Phe Pro Asp Ile Ser Ala Phe Ala His Ala Ala Pro Leu
            260                 265                 270

Pro Glu Ala Ala Asp Gly Thr Arg Leu Asp Asp Gln Pro Lys Ala Asp
        275                 280                 285

Val Leu Glu Ala His Glu Ala Glu Ala Glu Glu Pro Glu Ala Gly Lys
    290                 295                 300
```

Ser Glu Ala Glu Asp Asp Glu Asp Glu Val Asp Asp Leu Pro Ser Ser
305                 310                 315                 320

Arg Arg Pro Trp Arg Gly Pro Ile Ser Arg Lys Ala Ser Gln Thr Ser
            325                 330                 335

Val Tyr Leu Gln Glu Trp Asp Ile Pro Phe Glu Gln Val Glu Leu Gly
            340                 345                 350

Glu Pro Ile Gly Gln Gly Arg Trp Gly Arg Val His Arg Gly Arg Trp
            355                 360                 365

His Gly Glu Val Ala Ile Arg Leu Leu Glu Met Asp Gly His Asn Gln
    370                 375                 380

Asp His Leu Lys Leu Phe Lys Lys Glu Val Met Asn Tyr Arg Gln Thr
385                 390                 395                 400

Arg His Glu Asn Val Val Leu Phe Met Gly Ala Cys Met Asn Pro Pro
                405                 410                 415

His Leu Ala Ile Ile Thr Ser Phe Cys Lys Gly Arg Thr Leu His Ser
            420                 425                 430

Phe Val Arg Asp Pro Lys Thr Ser Leu Asp Ile Asn Lys Thr Arg Gln
            435                 440                 445

Ile Ala Gln Glu Ile Ile Lys Gly Met Gly Tyr Leu His Ala Lys Gly
    450                 455                 460

Ile Val His Lys Asp Leu Lys Ser Lys Asn Val Phe Tyr Asp Asn Gly
465                 470                 475                 480

Lys Val Val Ile Thr Asp Phe Gly Leu Phe Gly Ile Ser Gly Val Val
                485                 490                 495

Arg Glu Gly Arg Arg Glu Asn Gln Leu Lys Leu Ser His Asp Trp Leu
            500                 505                 510

Cys Tyr Leu Ala Pro Glu Ile Val Arg Glu Met Thr Pro Gly Lys Asp
            515                 520                 525

Glu Asp Gln Leu Pro Phe Ser Lys Ala Ala Asp Val Tyr Ala Phe Gly
    530                 535                 540

Thr Val Trp Tyr Glu Leu Gln Ala Arg Asp Trp Pro Leu Lys Asn Gln
545                 550                 555                 560

Ala Ala Glu Ala Ser Ile Trp Gln Ile Gly Ser Gly Glu Gly Met Lys
                565                 570                 575

Arg Val Leu Thr Ser Val Ser Leu Gly Lys Glu Val Ser Glu Ile Leu
            580                 585                 590

Ser Ala Cys Trp Ala Phe Asp Leu Gln Glu Arg Pro Ser Phe Ser Leu
            595                 600                 605

Leu Met Asp Met Leu Glu Lys Leu Pro Lys Leu Asn Arg Arg Leu Ser
    610                 615                 620

His Pro Gly His Phe Trp Lys Ser Ala Glu Leu
625                 630                 635

( 2 ) INFORMATION FOR SEQ ID NO:11:

( i ) SEQUENCE CHARACTERISTICS:
      ( A ) LENGTH: 326 amino acids
      ( B ) TYPE: amino acid
      ( C ) STRANDEDNESS: Not Relevant
      ( D ) TOPOLOGY: Not Relevant ( i i ) MOLECULE TYPE: peptide ( x i ) SEQUENCE DESCRIPTION: SEQ ID NO:11:

Asp Ala Lys Ser Ser Glu Glu Asn Trp Asn Ile Leu Ala Glu Glu Ile
1               5                   10                  15

Leu Ile Gly Pro Arg Ile Gly Ser Gly Ser Phe Gly Thr Val Tyr Arg

|   |   |   |   |   | 20 |   |   |   |   | 25 |   |   |   |   | 30 |   |   |
|---|---|---|---|---|---|---|---|---|---|---|---|---|---|---|---|---|---|
| Ala | His | Trp<br>35 | His | Gly | Pro | Val | Pro<br>40 | Val | Lys | Thr | Leu | Asn<br>45 | Val | Lys | Thr |
| Pro | Ser<br>50 | Pro | Ala | Gln | Leu | Gln<br>55 | Ala | Phe | Lys | Asn | Glu<br>60 | Val | Ala | Met | Leu |
| Lys<br>65 | Lys | Thr | Arg | His | Cys<br>70 | Asn | Ile | Leu | Ile | Phe<br>75 | Met | Gly | Cys | Val | Ser<br>80 |
| Lys | Pro | Ser | Leu | Ala<br>85 | Ile | Val | Thr | Gln | Trp<br>90 | Cys | Glu | Gly | Ser | Ser<br>95 | Leu |
| Tyr | Lys | His | Val<br>100 | His | Val | Ser | Glu | Thr<br>105 | Lys | Phe | Lys | Leu | Asn<br>110 | Thr | Leu |
| Ile | Asp | Ile<br>115 | Gly | Arg | Gln | Val | Ala<br>120 | Gln | Gln | Met | Asp | Tyr<br>125 | Leu | His | Ala |
| Lys | Asn<br>130 | Ile | Ile | His | Arg<br>135 | Asp | Leu | Lys | Ser | Asn<br>140 | Asn | Ile | Phe | Leu | His |
| Glu<br>145 | Asp | Leu | Ser | Val | Lys<br>150 | Ile | Gly | Asp | Phe | Gly<br>155 | Leu | Ala | Thr | Ala | Lys<br>160 |
| Thr | Arg | Trp | Ser | Gly<br>165 | Glu | Lys | Gln | Ala | Asn<br>170 | Gln | Pro | Thr | Gly | Ser<br>175 | Ile |
| Leu | Trp | Met | Ala<br>180 | Pro | Glu | Val | Ile | Arg<br>185 | Met | Gln | Glu | Leu | Asn<br>190 | Pro | Tyr |
| Ser | Phe | Gln<br>195 | Ser | Asp | Val | Tyr | Ala<br>200 | Phe | Gly | Ile | Val | Met<br>205 | Tyr | Glu | Leu |
| Leu | Ala<br>210 | Glu | Cys | Leu | Pro | Tyr<br>215 | Gly | His | Ile | Ser | Asn<br>220 | Lys | Asp | Gln | Ile |
| Leu<br>225 | Phe | Met | Val | Gly | Arg<br>230 | Gly | Leu | Leu | Arg | Pro<br>235 | Asp | Met | Ser | Gln | Val<br>240 |
| Arg | Ser | Asp | Ala | Arg<br>245 | Arg | His | Ser | Lys | Arg<br>250 | Ile | Ala | Glu | Asp | Cys<br>255 | Ile |
| Lys | Tyr | Thr | Pro<br>260 | Lys | Asp | Arg | Pro<br>265 | Leu | Phe | Arg | Pro | Leu<br>270 | Leu | Trp | Met |
| Leu | Glu | Asn<br>275 | Met | Leu | Arg | Thr<br>280 | Leu | Pro | Lys | Ile | His<br>285 | Arg | Ser | Ala | Ser |
| Glu | Pro<br>290 | Asn | Leu | Thr | Gln<br>295 | Ser | Gln | Leu | Gln | Asn<br>300 | Asp | Glu | Phe | Leu | Tyr |
| Leu<br>305 | Pro | Ser | Pro | Lys<br>310 | Thr | Pro | Val | Asn | Phe<br>315 | Asn | Asn | Phe | Gln | Phe<br>320 |
| Gly | Ser | Ala | Gly | Asn<br>325 | Ile |

( 2 ) INFORMATION FOR SEQ ID NO:12:

( i ) SEQUENCE CHARACTERISTICS:
        ( A ) LENGTH: 315 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:12:

| Gly<br>1 | Gln | Arg | Asp | Ser<br>5 | Ser | Tyr | Tyr | Trp | Glu<br>10 | Ile | Glu | Ala | Ser | Glu<br>15 | Val |
|---|---|---|---|---|---|---|---|---|---|---|---|---|---|---|---|
| Met | Leu | Ser | Thr<br>20 | Arg | Ile | Gly | Ser | Gly<br>25 | Ser | Phe | Gly | Thr | Val<br>30 | Tyr | Lys |
| Cys | Lys | Trp<br>35 | His | Gly | Asp | Val | Ala<br>40 | Val | Lys | Ile | Leu | Lys<br>45 | Val | Val | Asp |

| | | | | | | | | | | | | | | |
|---|---|---|---|---|---|---|---|---|---|---|---|---|---|---|
| Pro | Thr 50 | Pro | Glu | Gln | Phe | Gln 55 | Ala | Phe | Arg | Asn | Glu 60 | Val | Ala | Val | Leu |
| Arg 65 | Lys | Thr | Arg | His | Val 70 | Asn | Ile | Leu | Leu | Phe 75 | Met | Gly | Tyr | Met | Thr 80 |
| Lys | Asp | Asn | Leu | Ala 85 | Ile | Val | Thr | Gln | Trp 90 | Cys | Glu | Gly | Ser | Ser 95 | Leu |
| Tyr | Lys | His | Leu 100 | His | Val | Gln | Glu | Thr 105 | Lys | Phe | Gln | Met | Phe 110 | Gln | Leu |
| Ile | Asp | Ile 115 | Ala | Arg | Gln | Thr | Ala 120 | Gln | Gly | Met | Asp | Tyr 125 | Leu | His | Ala |
| Lys | Asn 130 | Ile | Ile | His | Arg | Asp 135 | Met | Lys | Ser | Asn | Asn 140 | Ile | Phe | Leu | His |
| Glu 145 | Gly | Leu | Thr | Val | Lys 150 | Ile | Gly | Asp | Phe | Gly 155 | Leu | Ala | Thr | Val | Lys 160 |
| Ser | Arg | Trp | Ser | Gly 165 | Ser | Gln | Gln | Val | Glu 170 | Gln | Pro | Thr | Gly | Ser 175 | Val |
| Leu | Trp | Met | Ala 180 | Pro | Glu | Val | Ile | Arg 185 | Met | Gln | Asp | Asn | Asn 190 | Pro | Phe |
| Ser | Phe | Gln 195 | Ser | Asp | Val | Tyr | Ser 200 | Tyr | Gly | Ile | Val | Leu 205 | Tyr | Glu | Leu |
| Met | Thr 210 | Gly | Glu | Leu | Pro | Tyr 215 | Ser | His | Ile | Asn | Asn 220 | Arg | Asp | Gln | Ile |
| Ile 225 | Phe | Met | Val | Gly | Arg 230 | Gly | Tyr | Ala | Ser | Pro 235 | Asp | Leu | Ser | Lys | Leu 240 |
| Tyr | Lys | Asn | Cys | Pro 245 | Lys | Ala | Met | Lys | Arg 250 | Leu | Val | Ala | Asp | Cys 255 | Val |
| Lys | Lys | Val | Lys 260 | Glu | Glu | Arg | Pro | Leu 265 | Phe | Pro | Gln | Ile | Leu 270 | Ser | Ser |
| Ile | Glu | Leu 275 | Leu | Gln | His | Ser | Leu 280 | Pro | Lys | Ile | Asn | Arg 285 | Ser | Ala | Ser |
| Glu | Pro 290 | Ser | Leu | His | Arg | Ala 295 | Ala | His | Thr | Glu | Asp 300 | Ile | Asn | Ala | Cys |
| Thr 305 | Leu | Thr | Thr | Ser | Pro 310 | Arg | Leu | Pro | Val | Phe 315 | | | | | |